United States Patent
Nakamura et al.

(10) Patent No.: US 7,781,599 B2
(45) Date of Patent: Aug. 24, 2010

(54) PROCESS FOR PRODUCTION OF AROMATIC COMPOUNDS

(75) Inventors: Masaharu Nakamura, Uji (JP); Eiichi Nakamura, Tokyo (JP); Keiko Matsuo, Tokyo (JP); Shingo Ito, Uji (JP)

(73) Assignee: Japan Science and Technology Agency, Saitama (JP)

( * ) Notice: Subject to any disclaimer, the term of this patent is extended or adjusted under 35 U.S.C. 154(b) by 1049 days.

(21) Appl. No.: 10/588,552

(22) PCT Filed: Feb. 10, 2005

(86) PCT No.: PCT/JP2005/002529

§ 371 (c)(1),
(2), (4) Date: Aug. 7, 2006

(87) PCT Pub. No.: WO2005/075384

PCT Pub. Date: Aug. 18, 2005

(65) Prior Publication Data

US 2007/0123734 A1    May 31, 2007

(30) Foreign Application Priority Data

Feb. 10, 2004  (JP) .............................. 2004-033941
Sep. 28, 2004  (JP) .............................. 2004-282578

(51) Int. Cl.
- C07C 2/02 (2006.01)
- C07C 5/00 (2006.01)
- C07C 69/76 (2006.01)
- C07D 209/04 (2006.01)

(52) U.S. Cl. ...................... 548/511; 560/103; 585/375; 585/446; 585/462

(58) Field of Classification Search .................. 560/103; 548/511; 585/375, 446, 462
See application file for complete search history.

(56) References Cited

U.S. PATENT DOCUMENTS

2003/0220498 A1    11/2003    Furstner et al.

FOREIGN PATENT DOCUMENTS

| JP | 2000-229243 A | 8/2000 |
| JP | 2000-344727 A | 12/2000 |
| JP | 2001-293375 A | 10/2001 |

OTHER PUBLICATIONS

Martin et al., "Cross-Coupling of Alkyl Halides with Aryl Grignard Reagents Catalyzed by a Low-Valent Iron Complex," Angew. Chem. Int. Ed., Jul. 26, 2004, vol. 43, No. 30, pp. 3955-3957.

Nagano et al., "Iron-Catalyzed Grignard Cross-Coupling with Alkyl Halides Possessing β-Hydrogens," Organic Letters, 2004, 6(8):1297-1299.

Nakamura et al., "Iron-Catalyzed Cross-Coupling of Primary and Secondary Alkyl Halides with Aryl Grignard Reagents," J. Am. Chem. Soc., 2004, 126(12):3686-3687.

Primary Examiner—Peter G O'Sullivan
(74) Attorney, Agent, or Firm—Foley & Lardner LLP

(57) ABSTRACT

A problem of the present invention is to provide an economical process with minimized toxicity for producing an aromatic compound having a variety of substituents such as various alkyl groups, and the problem is solved by a process for production of an aromatic compound represented by formula (1) below, which comprises reacting a compound represented by formula (2) below with an aromatic magnesium reagent represented by formula (3a) below in the presence of an iron catalyst and a diamine compound:

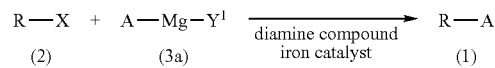

wherein R is an optionally substituted hydrocarbon group or a $C_3$-$C_{10}$ saturated or unsaturated ring group; A is an optionally substituted $C_4$-$C_{20}$ aromatic group or an optionally substituted heteroaromatic group; X is a halogen atom or a sulfonic acid ester; and $Y^1$ is bromine, iodine, chlorine or a carbanion ligand.

21 Claims, No Drawings

PROCESS FOR PRODUCTION OF AROMATIC COMPOUNDS

This application is a National Stage application of PCT/JP2005/002529, filed Feb. 10, 2005, which claims priority from Japanese patent applications JP 2004-033941, filed Feb. 10, 2004 and JP 2004-282578, filed Sep. 28, 2004. The entire contents of each of the aforementioned applications are incorporated herein by reference.

TECHNICAL FIELD

The present invention relates to a process for production of aromatic compounds, and more particularly relates to a process for production of aromatic compounds which involves the cross-coupling reaction of aliphatic organic compounds such as alkyl halides, etc. and aromatic organometallic reagents using iron catalysts.

BACKGROUND ART

Alkylated aromatic compounds, in particular, a group of aromatic compounds having a secondary alkyl group on the aromatic ring are known to be useful as intermediates for chemical products including medical drugs, agricultural chemicals, etc., as raw materials for liquid crystals, and so on.

As a process for site-selective production of aromatic compounds having a secondary alkyl group, a coupling reaction of alkyl magnesium reagents with aryl halides or aryl sulfonates in the presence of a nickel or palladium catalyst was hitherto known (Hayashi, T.; Konishi, M.; Kobori, Y.; Kumada, M.; Higuchi, T.; Hirotsu, K.; *J. Am. Chem. Soc.* 1984, 106, 158-163, Ogasawara, M.; Yoshida, K.; Hayashi, T.; *Organometallics*, 2000, 19, 1567-1571, Doherty, S.; Knight, J.; Robins, E. G.; Scanlan, T. H.; Champkin, P. A. Clegg, W.; *J. Am. Chem. Soc.* 2001, 123, 5110-5111).

However, this process essentially requires addition of a phosphine ligand having a complicated structure and is further accompanied by isomerization of the secondary alkyl group into a primary alkyl group, depending upon structure of the secondary alkyl group, which results in a problem that the objective product cannot be obtained in a high yield. Another problem is that highly toxic or expensive catalysts such as a nickel catalyst or a palladium catalyst are required and hence, the process cannot be applied to mass production in the fields of medical drugs or agricultural chemicals where use of highly toxic reagents should be avoided.

As processes for producing aromatic compounds having alkyl groups from alkyl halides or alkyl sulfonates and aromatic organometallic reagents, a cross-coupling of alkyl sulfonates or alkyl halides with aromatic magnesium reagents in the presence of a diene ligand using palladium as a catalyst (Terao, J.; Naitoh, Y.; Kuniyasu, H.; Kambe, N.; *Chem. Lett.* 2003, 32, 890-901) and a process for catalytic cross-coupling of alkyl halides with aromatic magnesium reagents in the presence of a diene ligand using copper or nickel as a catalyst are also known (Terao, J.; Ikumi, A.; Kuniyasu, H.; Kambe, N.; *J. Am. Chem. Soc.* 2003, 125, 5646-5647).

In addition, a palladium-catalyzed cross-coupling reaction of alkyl halides with aromatic zinc compounds, aromatic tin compounds or aromatic silicon compounds in the presence of a bulky phosphine ligand such as tricyclohexylphosphin is also known (Zhou, J.; Fu, G. C.; *J. Am. Chem. Soc.* 2003, 125, 12527-12530, Tang, H.; Menzel, K.; Fu, G. C.; *Angew. Chem., Int. Ed.* 2003, 42, 5079-5082, Lee, J.-Y.; Fu, G. C.; *J. Am. Chem. Soc.* 2003, 125, 5616-5617).

In the case of introducing a secondary alkyl group by these processes, however, alkenes are produced by side-reactions such as an elimination reaction to give the objective product only in a poor yield, and these processes involve a problem that they are not available for synthesis of aromatic compounds having a secondary alkyl substituent(s).

As a process for producing aromatic compounds having an alkyl group from secondary alkyl halides and aromatic organometallic compounds, there is also known a process which comprises catalytic cross-coupling of aromatic boron compounds with secondary alkyl halides using a nickel catalyst (Zhou, J.; Fu, G. C.; *J. Am. Chem. Soc.* 2004, 126, 1340-1341). In this process, aromatic compounds having various secondary alkyl substituents can be synthesized but the problem that highly toxic nickel should be used still remains unsolved.

Also, a cross-coupling reaction of an unsaturated organic halide such as an aryl halide or alkenyl halide or an electrophilic reagent such as allyl phosphate, etc. with an aromatic or alkyl magnesium reagent, a zinc reagent or a manganese reagent is known as a process using an inexpensive and low-toxic iron catalyst as a catalyst (Fürstner, A.; Leitner; *A. Angew. Chem., Int. Ed.* 2002, 41, 609-612, Fürstner, A.; Leitner, A.; Mendez, M.; Krause, H.; *J. Am. Chem. Soc.* 2002, 124, 13856-13863, Pre-Grant patent Publication No. 2003/0220498).

According to this process, it is possible to synthesize an aromatic compound having a secondary alkyl substituent from a secondary alkyl magnesium reagent and an aryl halide. However, the process involves such disadvantages that many functional groups including carbonyl, cyano, etc. cannot be present concurrently upon preparation of the secondary alkyl magnesium reagent. Moreover, the yield is as low as 50%-60%, which is unsuited for a process for producing a variety of alkylated aromatic compounds. Further when an alkyl halide and an aromatic magnesium reagent are used under the reaction conditions of this process, olefins are predominantly formed by side reactions such as elimination, etc., and the process is disadvantageous in that the objective product is produced only in a poor yield.

A process which comprises a coupling reaction of an alkyl halide with an aromatic magnesium reagent using an iron complex catalyst having a catalytic amount of N,N,N',N'-tetramethylethylenediamine (TMEDA) as a ligand is also known (Martin, R.: Fürstner, A.; *Angew. Chem., Int. Ed.* 2004, 43, 3955-3957). According to this process, however, there was a problem that the reaction did not proceed at all when the chloride or fluoride was used as the alkyl halide.

Moreover, a process which involves coupling as in the process described above, except for using a trivalent iron acetylacetonate complex as the catalyst, using no diamine ligand and changing the solvent from tetrahydrofuran (THF) to diethyl ether, is also known (Nagano, T.; Hayashi, T.; *Org. Lett.* 2004, 6, 1297-1299). However, this process was also disadvantageous in that the reaction did not proceed at all when the chloride or fluoride was used as the alkyl halide. In addition, the process involved another problem that the yield is generally poor and not practical.

It would be desired to provide a highly safe process capable of mass production, which can produce aromatic compounds having a variety of primary or secondary alkyl substituents in a high yield.

DISCLOSURE OF INVENTION

An object of the present invention is to provide a practical process for production of aromatic compounds having a wide variety of alkyl substituents using a low-toxic, inexpensive and readily available iron catalyst.

In other words, a first embodiment of the present invention relates to a process for production of an aromatic compound represented by formula (1) below:

$$R\text{-}A \tag{1}$$

wherein, R is an optionally substituted hydrocarbon group or a $C_3$-$C_{10}$ saturated or unsaturated ring group, which ring may optionally be intervened by an oxygen atom or a group represented by formula —N(B)— (wherein B is a hydrogen atom, an optionally substituted $C_1$-$C_{10}$ hydrocarbon group or an optionally substituted $C_1$-$C_{10}$ alkoxycarbonyl group) and may optionally be substituted; and A is an optionally substituted $C_4$-$C_{20}$ aromatic group or an optionally substituted heteroaromatic group, which comprises reacting a compound represented by formula (2) below:

$$R\text{—}X \tag{2}$$

wherein, R has the same significance as described above, and X is a halogen atom or a sulfonic acid ester, with an aromatic magnesium reagent represented by formula (3a) below:

$$A\text{-}Mg\text{—}Y^1 \tag{3a}$$

wherein A has the same significance as described above and $Y^1$ is bromine, iodine, chlorine or a carbanion ligand, in the presence of an iron catalyst and a diamine compound.

A second embodiment of the present invention provides a process for production of the aromatic compound represented by formula (1) described above, which comprises:

a step of reacting the aromatic magnesium reagent represented by formula (3a) below:

$$A\text{-}Mg\text{—}Y^1 \tag{3a}$$

wherein A has the same significance as described above and $Y^1$ is bromine, iodine, chlorine or a carbanion ligand, with a zinc compound represented by formula (4b) below:

$$Z^3\text{—}Zn\text{—}Z^4 \tag{4b}$$

wherein each of $Z^3$ and $Z^4$, which may be the same or different, independently represents bromine, iodine, chlorine, fluorine or a trifluoromethanesulfonyl group, in the presence of a diamine compound to give the reaction mixture; and a step of reacting the reaction mixture with a compound represented by formula (2) below:

$$R\text{—}X \tag{2}$$

wherein R has the same significance as described above and X is a halogen atom or a sulfonic acid ester, in the presence of an iron catalyst.

A third embodiment of the present invention provides a process for production of the aromatic compound represented by formula (1) described above, which comprises:

a step of reacting an aromatic lithium reagent represented by formula (3c) below:

$$A\text{-}Li \tag{3c}$$

wherein A has the same significance as described above, with a zinc compound represented by formula (4b) below:

$$Z^3\text{—}Zn\text{—}Z^4 \tag{4b}$$

wherein each of $Z^3$ and $Z^4$, which may be the same or different, independently represents bromine, iodine or chlorine, in the presence of a diamine compound and then reacting with a Lewis acid metal compound containing at least one metal selected from magnesium, titanium, zirconium, hafnium, gallium and aluminum to give the reaction mixture, and a step of reacting the reaction mixture with a compound represented by formula (2) below:

$$R\text{—}X \tag{2}$$

wherein R has the same significance as described above and X is a halogen atom or a sulfonic acid ester, in the presence of an iron catalyst.

A fourth embodiment of the present invention provides a process for production of the aromatic compound represented by formula (1) above, which comprises:

a step of reacting an aromatic zinc reagent represented by formula (3b) below:

$$A\text{-}Zn\text{—}Y^2 \tag{3b}$$

wherein A has the same significance as described above and $Y^2$ is bromine, iodine or chlorine, with a magnesium compound represented by formula (4a) below:

$$Z_1\text{-}Mg\text{—}Z^2 \tag{4a}$$

wherein $Z^1$ is a carbanion ligand and $Z^2$ is bromine, iodine or chlorine, in the presence of a diamine compound to give the reaction mixture; and a step of reacting the reaction mixture with a compound represented by formula (2) below:

$$R\text{—}X \tag{2}$$

wherein R has the same significance as described above and X is a halogen atom or a sulfonic acid ester, in the presence of an iron catalyst.

In the first to fourth embodiments of the present invention, the iron catalyst is preferably an iron salt or an iron complex.

Further in the first to fourth embodiments of the present invention, the diamine compound is preferably a bidentate ligand.

In the first to fourth embodiments of the present invention, R is preferably an optionally substituted primary alkyl group or an optionally substituted secondary alkyl group.

In the first to fourth embodiments of the present invention, A is preferably an optionally substituted $C_4$-$C_{20}$ aryl group.

In the third embodiment of the present invention, the Lewis acidic metal complexes may also be a metal compound represented by formula (4c) below:

$$M(Z_1)_n \tag{4c}$$

wherein M is magnesium, titanium, zirconium, hafnium, gallium or aluminum; each of $Z_1$, which may be the same or different, independently represents bromine, iodine, chlorine or a carbanion ligand; and n is an integer of 2 to 4.

According to the present invention, aromatic compounds having various substituents such as a wide variety of alkyl groups can be produced economically in a high yield under environmental conditions with minimized toxicity. Thus, aromatic compounds having a desired substituent(s) can be mass-produced in the fields of medical drugs and agricultural chemicals where use of highly toxic reagents should be avoided.

Also, high chemoselectivity enables to efficiently introduce a heteroaromatic ring into a protected sugar, which is also applicable to synthesis of, e.g., C-arylglycosides.

Furthermore, the halogen atom in polymers such as polyvinyl chloride, etc. can be converted into a desired aromatic substituent so that the present invention can be used for polymer modification.

BEST MODE FOR CARRYING OUT THE INVENTION

According to the first embodiment of the present invention, there is provided a process for production of the aromatic compound represented by formula (1) below, which comprises reacting the compound represented by formula (2) below with the aromatic magnesium reagent represented by formula (3a) below, in the presence of the iron catalyst and the diamine compound.

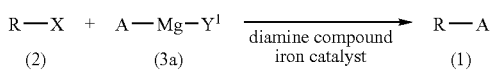

In the first embodiment of the present invention, the compound represented by formula (2) is employed.

R is an optionally substituted hydrocarbon group or a $C_3$-$C_{10}$ saturated or unsaturated ring group.

The "hydrocarbon group" may be a relatively low molecular weight hydrocarbon group up to about $C_{30}$ or may be a higher hydrocarbon group having more carbon atoms.

The ring described above may optionally be intervened by an oxygen atom or a group represented by formula —N(B)— (wherein B is a hydrogen atom, an optionally substituted $C_1$-$C_{10}$ hydrocarbon group or an optionally substituted $C_1$-$C_{10}$ alkoxycarbonyl group), and may optionally be substituted.

The optionally substituted high molecular hydrocarbon is, for example, a monovalent group formed by eliminating one optional halogen atom from a polymer such as polyvinyl chloride, etc.

The optionally substituted low molecular weight hydrocarbon group is, for example, a $C_2$-$C_{30}$ hydrocarbon group.

In the first embodiment of the present invention, the hydrocarbon group of "$C_2$-$C_{30}$ hydrocarbon group" shown by R may be either a saturated or unsaturated acyclic group or a saturated or unsaturated ring group. When the $C_2$-$C_{30}$ hydrocarbon group is acyclic, the group may be linear or branched. The "$C_2$-$C_{30}$ hydrocarbon group" includes a $C_2$-$C_{30}$ alkyl group, a $C_3$-$C_{30}$ alkenyl group, a $C_3$-$C_{30}$ alkynyl group, a $C_5$-$C_{30}$ alkyldienyl group, a $C_7$-$C_{30}$ arylalkyl group, a $C_3$-$C_{30}$ cycloalkyl group, a $C_3$-$C_{30}$ cycloalkenyl group, a ($C_3$-$C_{15}$ cycloalkyl) $C_1$-$C_{15}$ alkyl group, a condensed polycyclic group, etc.

In the first embodiment of the present invention, the "$C_2$-$C_{30}$ alkyl group" shown by R is preferably a $C_2$-$C_{15}$ alkyl group, more preferably a $C_4$-$C_{12}$ alkyl group. Examples of the alkyl group are not particularly limited to, but include propyl, isopropyl, n-butyl, sec-butyl, tert-butyl, pentyl, hexyl, dodecenyl, etc.

In the first embodiment of the present invention, the "$C_3$-$C_{30}$ alkenyl group" shown by R is preferably a $C_3$-$C_{15}$ alkenyl group, more preferably a $C_4$-$C_{10}$ alkenyl group. Examples of the alkenyl group are not particularly limited to, but include 2-propenyl, 2-methyl-2-propenyl, 2-methylallyl, 2-butenyl, 3-butenyl, 4-pentenyl, and the like.

In the first embodiment of the present invention, the "$C_3$-$C_{30}$ alkynyl group" shown by R is preferably a $C_3$-$C_{15}$ alkynyl group, more preferably a $C_4$-$C_{10}$ alkynyl group. Examples of the alkynyl group are not particularly limited to, but include 3-butynyl, 4-pentynyl, etc.

In the first embodiment of the present invention, the "$C_5$-$C_{30}$ alkyldienyl group" shown by R is preferably a $C_5$-$C_{15}$ alkyldienyl group, more preferably a $C_6$-$C_{10}$ alkyldienyl group. Examples of the alkyldienyl group are not particularly limited to, but include 3,5-hexadienyl, etc.

In the first embodiment of the present invention, the "$C_7$-$C_{30}$ arylalkyl group" shown by R is preferably a $C_7$-$C_{12}$ arylalkyl group. Examples of the arylalkyl group are not particularly limited to, but include benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc. Preferred are 2,2-diphenylethyl, 3-phenylpropyl, 4-phenylbutyl and 5-phenylpentyl.

In the first embodiment of the present invention, the "$C_3$-$C_{30}$ cycloalkyl group" shown by R is preferably a $C_3$-$C_{10}$ cycloalkyl group. Examples of the cycloalkyl group are not particularly limited to, but include cyclopropyl, cyclobutyl, cyclopentyl, cyclohexyl, etc.

In the first embodiment of the present invention, the "$C_3$-$C_{30}$ cycloalkenyl group" shown by R is preferably a $C_3$-$C_{10}$ cycloalkenyl group. Examples of the cycloalkenyl group are not particularly limited to, but include cyclopropenyl, cyclobutenyl, cyclopentenyl, cyclohexenyl, etc.

In the first embodiment of the present invention, the "condensed polycyclic group" shown by R includes a monovalent group formed by eliminating one optional hydrogen atom from a condensed polycyclic ring.

In the first embodiment of the present invention, the "$C_3$-$C_{10}$ saturated ring group or unsaturated ring group" shown by R includes a monocyclic group, a condensed polycyclic group, etc.

The "monocyclic group" is, for example, a monovalent group formed by eliminating optional one hydrogen atom from a 3-membered to 7-membered ring, such a monovalent group-$C_1$-$C_6$ alkyl group, etc.

The "condensed polycyclic group" is, for example, a monovalent group formed by eliminating optional one hydrogen atom from a condensed multi-ring, such a monovalent group-$C_1$-$C_6$ alkyl group, etc.

In the first embodiment of the present invention, the "$C_3$-$C_{10}$ saturated group or unsaturated ring group" is preferably a 5-membered to 7-membered monocyclic ring group, which ring may optionally be intervened by an oxygen atom or a group represented by formula —N(B)— (wherein B is a hydrogen atom, an optionally substituted $C_1$-$C_{10}$ hydrocarbon group (e.g., methyl, ethyl, propyl, isopropyl, n-butyl, sec-butyl, tert-butyl, pentyl, hexyl, phenyl, etc.) or an optionally substituted $C_1$-$C_{10}$ alkoxycarbonyl group), more preferably, piperidinyl, tetrahydropyranyl or tetrahydropyranylmethyl.

In the first embodiment of the present invention, a substituent(s) may be introduced into the "hydrocarbon group" or "$C_3$-$C_{10}$ saturated ring group or unsaturated ring group" shown by R, or into the "$C_1$-$C_{10}$ hydrocarbon group" and "$C_1$-$C_{10}$ alkoxycarbonyl group" shown by B when R is the "$C_3$-$C_{10}$ saturated ring group or unsaturated ring group, which ring may optionally be intervened by the group represented by formula —N(B)—." The substituent(s) are preferably those that do not react with the aromatic magnesium reagent.

Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.), a $C_2$-$C_{20}$ alkenyl-$C_1$-$C_{20}$ alkyl-$C_1$-$C_{20}$ alkoxy (e.g., 1-vinyl-1-methylethoxy, etc.);

a protected hydroxy group (—OB$^3$: wherein B$^3$ is an alkyl group, an arylalkyl group, an ether-substituted arylalkyl group, an ether-substituted alkyl group, or a silyl group which may be optionally substituted with a C$_1$-C$_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

a trialkylsilyl group (—B$^4$: wherein B$^4$ is a silyl group, which may optionally be substituted with a C$_1$-C$_6$ hydrocarbon group (e.g., methyl, ethyl, propyl, isopropyl, n-butyl, sec-butyl, tert-butyl, pentyl, hexyl, phenyl, etc.). Examples of the trialkylsilyl group include trimethylsilyl, dimethyl tert-butylsilyl, triethylsilyl, tert-butyldiphenylsilyl, etc.);

an acetal group (—CB$^5$(OB$^6$)(OB$^7$): wherein B$^5$ is a hydrogen atom or an optionally substituted C$_1$-C$_6$ alkyl group; each of B$^6$ and B$^7$, which may be the same or different, independently represents an optionally substituted C$_1$-C$_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of B$^6$ and B$^7$ are a methyl group, an ethyl group, etc. and when they are cross-bridged with one another, examples include an ethylene group, a trimethylene group, etc.); a N-indolyl; a C$_1$-C$_{10}$ alkoxy group (e.g., methoxy, ethoxy, propoxy, butoxy, etc.); a C$_6$-C$_{10}$ aryloxy group (e.g., phenyloxy, naphthyloxy, biphenyloxy, etc.); a halogen atom (e.g., fluorine, chlorine, bromine, iodine); an amido group; an amino group, or the like.

Examples of substituents which are somewhat reactive with the aromatic magnesium reagent to reduce the yield but can be introduced include:

a C$_6$-C$_{20}$ aryl-C$_1$-C$_{20}$ alkyloxycarbonyl (e.g., benzyloxycarbonyl, etc.); a C$_1$-C$_{20}$ alkyl-carbonyloxy (e.g., acetoxy, propanoyloxy, pivaloyloxy, etc.); ethoxycarbonyl, and the like.

One or more of the substituents above may be introduced at a substitutable position(s). For example, 1 to 4 substituents may be introduced. Where the number of substituents is 2 or more, the respective substituents may be the same or different.

In the first embodiment of the present invention, examples of the "optionally substituted condensed polycyclic ring" are not particularly limited to, but include those having a steroid skeleton such as cholestane, etc.

In the first embodiment of the present invention, R is preferably an optionally substituted primary alkyl group or an optionally substituted secondary alkyl group.

The "optionally substituted primary alkyl group" is preferably 3-N-indolylpropyl, ethoxycarbonylpentyl, octyl, etc.

The "optionally substituted secondary alkyl group" is preferably sec-butyl, cyclohexyl, 4-tert-butylcyclohexyl, cycloheptyl, 2-norbornyl, etc.

In the first embodiment of the present invention, the substituents introduced into the "primary alkyl group" and "secondary alkyl group," which are acceptable as R, are particularly preferably a methoxycarbonyl group, an ethoxycarbonyl group, a tert-butoxycarbonyl group, an alkenyl group, an alkynyl group, a 3-N-indolyl group, an alkyl ether, a silyl ether, a tertiary amino group, a secondary amido group or an acetal.

In the formula (2) described above, X is a halogen atom or a sulfonic acid ester (R'—S(O)$_2$—O—). The halogen atom is preferably bromine, iodine or chlorine. The sulfonic acid ester is preferably a p-toluenesulfonic acid ester.

In the first embodiment of the present invention, X is preferably a halogen atom, more preferably, iodine bromine or chlorine.

In the process for production of the aromatic compounds in accordance with the first embodiment of the present invention, the aromatic magnesium reagents represented by formula (3a) below are employed.

A-Mg—Y$^1$ (3a)

In formula (3a) above, A is an optionally substituted C$_4$-C$_{20}$ aromatic group or an optionally substituted heteroaromatic group.

In the specification, the "aromatic group" includes a monocyclic aromatic group and a polycyclic aromatic group.

The "monocyclic aromatic group" is a monovalent group formed by eliminating optional one hydrogen atom from, e.g., a benzene ring or a 5-membered or 6-membered aromatic heterocyclic ring, etc.

Examples of the "5-membered or 6-membered aromatic heterocyclic ring" include furan, thiophene, pyrrole, pyrane, thiopyrane, pyridine, thiazole, imidazole, pyrimidine, 1,3,5-triazine, etc.

The "polycyclic aromatic group" includes a monovalent group formed by eliminating optional one hydrogen group from a polycyclic aromatic hydrocarbon or a polycyclic heteroaromatic ring.

The "polycyclic aromatic hydrocarbon" includes biphenyl, triphenyl, naphthalene, indene, anthracene, phenanthrene, etc.

The polycyclic heteroaromatic ring" includes indole, quinoline, purine, etc.

In the specification, the "heteroaromatic group" includes a monovalent group formed by eliminating optional one hydrogen group from a 5-membered to 7-membered aromatic heterocyclic ring containing at least one hetero atom selected from a nitrogen atom, a sulfur atom and an oxygen atom, in addition to carbon atoms, etc.; and the like.

Examples of the "heteroaromatic group" include a pyridyl such as 2-, 3- or 4-pyridyl, etc., a benzofuranyl such as 2-benzofuranyl, 3-benzofuranyl, etc., an indolyl such as 2-indolyl, 3-indolyl, etc. a pyrimidyl group, etc.

In the specification, a substituent(s) may be introduced into the "C$_4$-C$_{20}$ aromatic group" or "heteroaromatic group." The substituents are preferably those that do not react with the aromatic magnesium reagents. Examples of the substituents include:

an optionally substituted C$_1$-C$_{10}$ alkyl group (e.g., methyl, ethyl, propyl, butyl, trifluoromethyl, etc.);

a C$_2$-C$_{10}$ alkenyl group (e.g., vinyl, allyl, propenyl, isopropenyl, 2-methyl-1-propenyl, 2-methylallyl, 2-butenyl, etc.);

a C$_2$-C$_{20}$ alkynyl group (e.g., ethynyl, propynyl, butynyl, etc.);

a protected hydroxy group (—OB$^3$: wherein B$^3$ is an alkyl group, an arylalkyl group, an ether-substituted arylalkyl group, an ether-substituted alkyl group, or a silyl group which may be optionally substituted with a C$_1$-C$_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

an acetal group (—CB$^5$(OB$^6$)(OB$^7$): wherein B$^5$ is a hydrogen atom or an optionally substituted C$_1$-C$_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amino group, or the like.

In this case, one or more of the substituents above may be introduced at a substitutable position(s). For example, 1 to 4 substituents may be introduced. Where the number of substituents is 2 or more, the respective substituents may be the same or different.

The substituents cross-bridged with one another may be introduced into 2 or more substitutable positions and examples of such substituents include methylenedioxy, ethylenedioxy, tetramethylethylenedioxy, propylenedioxy groups, etc.

In the first embodiment of the present invention, A is preferably an optionally substituted phenyl group, more preferably phenyl, 2-methylphenyl, 4-methylphenyl, 4-methoxyphenyl or 3,4-(methylenedioxy)phenyl.

In formula (3a) described above, $Y^1$ is bromine, iodine, chlorine or a carbanion ligand.

In the specification, the "carbanion ligand" includes an optionally substituted phenyl group, propynyl group ($CH_3C\equiv C$—), phenylethynyl group ($PhC\equiv C$—), trimethylsilylmethyl group ($Me_3SiCH_2$—), etc.

In the first embodiment of the present invention, when $Y^1$ is the "phenyl group," a substituent(s) may be introduced into the phenyl group. Examples of the substituents include a $C_1$-$C_{10}$ alkyl group (e.g., methyl, ethyl, propyl, butyl, trifluoromethyl, etc.), a $C_1$-$C_{10}$ alkoxy group (e.g., methoxy, ethoxy, propoxy, butoxy, etc.), and the like. In this case, one or more of the substituents may be introduced at a substitutable position(s). For example, 1 to 4 substituents may be introduced. Where the number of substituents is 2 or more, the respective substituents may be the same or different.

Furthermore, the substituents cross-bridged with one another may be introduced into 2 or more substitutable positions forming a ring and examples of such substituents include methylenedioxy, ethylenedioxy, tetramethylethylenedioxy, propylenedioxy groups, etc.

In the first embodiment of the present invention, $Y^1$ is preferably bromine.

In the first embodiment of the present invention, the amount of the aromatic magnesium reagent represented by formula (3a) described above is at least 1 mol equivalent, preferably 1.1 to 2 mol equivalents, based on 1 mol of the compound represented by formula (2) above.

In the process for production of the aromatic compounds in accordance with the first embodiment of the present invention, the iron catalyst which is inexpensive and low toxic are employed.

The iron catalyst used in the first embodiment of the present invention may be an iron salt or an iron complex.

Where the iron catalyst is an iron salt, the salt of iron with an inorganic acid such as hydrochloric acid, sulfuric acid, etc. can be employed. For example, an iron (III) halide is preferred. In particular, an iron (III) salt such as $FeCl_3$ is preferably employed.

Where the iron catalyst is an iron complex, a carbonyl, a halogen atom, a Schiff's base, a polyamine, dimethylformamide or the like is employed as the ligand. The central metal is preferably tetra- to hexa-coordination. Specifically, iron complexes such as a monovalent carbonyl complex $[FeCp(CO)_2]_2$ (formula 1 below), a bivalent neutral Schiff's base complex (formula 2 below), a trivalent cationic tetramine complex (formula 3 below) or a trivalent dimethylformamide complex (formula 4 below) can be preferably employed.

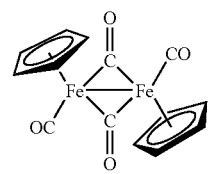

1

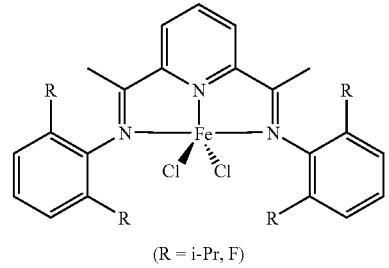

(R = i-Pr, F)

2

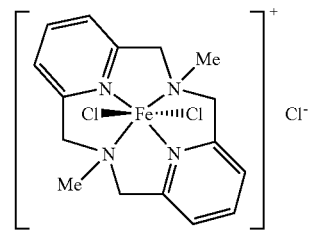

3

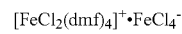

$[FeCl_2(dmf)_4]^+ \cdot FeCl_4^-$

4

In the first embodiment of the present invention, the iron catalyst is preferably an iron salt, more preferably $FeCl_3$.

In the first embodiment of the present invention, the amount of the iron catalyst is preferably 0.001 to 0.5 mol equivalent, preferably 0.01 to 0.1 mol equivalent and more preferably 0.03 to 0.07 mol equivalent, based on 1 mol of the compound represented by formula (2) described above.

In the process for production of the aromatic compounds in accordance with the first embodiment of the present invention, the diamine compound is used.

By using the diamine compound in the first embodiment of the present invention, the formation of by-products by side reactions can be minimized as less as possible so that the objective product can be obtained in a high yield.

The diamine compound is preferably a bidentate ligand, more preferably an ethylenediamine which may optionally have a substituent such as N,N,N',N'-tetramethylethylenediamine (TMEDA), etc.

In the first embodiment of the present invention, the amount of the diamine compound is 0.5 to 10 mol equivalents, preferably 1 to 3 mol equivalents and most preferably 1 to 2 mol equivalents, based on 1 mol of the compound represented by formula (2) described above.

In the first embodiment of the present invention, typically the aromatic magnesium reagent represented by formula (3a) described above and the diamine compound described above are added to a solution containing the compound represented by formula (2) above and the iron catalyst described above, and the mixture is stirred. Alternatively, the aromatic magnesium reagent represented by formula (3a) described above is added to a solution containing the compound represented by formula (2) above, the iron catalyst described above and the diamine compound described above, followed by stirring.

Preferably, the addition is achieved by dropwise adding them gradually in any case, in view of enhancing the yield. The rate of dropwise addition may vary depending upon a scale of the reaction but when the amount of the compound represented by formula (2) above is approximately 50 mmol, it is preferred to add the solution of the aromatic magnesium reagent (3a) at a rate of about 1 mmol/min. When the amount of the compound represented by formula (2) above is approximately 1 mmol, it is preferred to add the solution of the compound shown by the aromatic magnesium reagent (3a) at a rate of about 0.06 mmol/min.

In the first embodiment of the present invention, the reaction is carried out preferably in a temperature range of −10° C. to 50° C., more preferably in a temperature range of 0° C. to 30° C. The pressure is preferably under normal pressure.

In the first embodiment of the present invention, the solvent is preferably a solvent which can dissolve the compound represented by formula (2) above. An aliphatic or aromatic organic solvent is used as the solvent. For example, an ethereal solvent such as tetrahydrofuran, diethyl ether, etc.; an aromatic hydrocarbon such as toluene, etc. is used.

According to the second embodiment of the present invention, there is provided a process for production of the aromatic compound represented by formula (1) below, which comprise the step of reacting the aromatic magnesium reagent represented by formula (3a) described below with the zinc compound represented by formula (4b) in the presence of the diamine compound to give the reaction mixture and the step of reacting the reaction mixture above with the compound represented by formula (2) below in the presence of the iron catalyst.

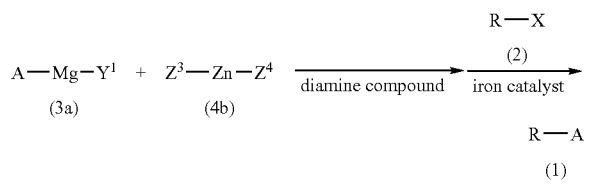

wherein R, X, $Y^1$ and A have the same significance as described above.

In the second embodiment of the present invention, the compound represented by formula (2) below is employed.

In the formula above, R and X are the same as those described in the first embodiment of the present invention.

In the second embodiment of the present invention, a substituent(s) may be introduced into the "hydrocarbon group" or "$C_3$-$C_{10}$ saturated ring group or unsaturated ring group" shown by R, or into the "$C_1$-$C_{10}$ hydrocarbon group" and "$C_1$-$C_{10}$ alkoxycarbonyl group" shown by B when R is the "$C_3$-$C_{10}$ saturated ring group or unsaturated ring group, which ring may optionally be intervened by the group represented by formula —N(B)—." The substituent(s) are preferably those that do not react with the organozinc reagent obtained by reacting the aromatic magnesium reagent represented by formula (3a) described above with the zinc compound represented by formula (4b) described above. Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.);

a $C_2$-$C_{20}$ alkenyl-$C_1$-$C_{20}$ alkyl-$C_1$-$C_{20}$ alkoxy (e.g., 1-vinyl-1-methylethoxy, etc.);

a $C_6$-$C_{20}$ aryl-$C_1$-$C_{20}$ alkyloxycarbonyl (e.g., benzyloxycarbonyl, etc.);

a $C_1$-$C_{20}$ alkyl-carbonyloxy (e.g., acetoxy, propanoyloxy, pivaloyloxy, etc.);

a protected hydroxy group (—$OB^3$: wherein $B^3$ is an alkyl group, an arylalkyl group, an ether-substituted arylalkyl group, an ether-substituted alkyl group, or a silyl group which may be optionally substituted with a $C_1$-$C_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

a trialkylsilyl group (—$B^4$: wherein $B^4$ is an optionally substituted silyl group, which may optionally be substituted with a $C_1$-$C_6$ hydrocarbon group (e.g., methyl, ethyl, propyl, isopropyl, n-butyl, sec-butyl, tert-butyl, pentyl, hexyl, phenyl, etc.), etc. Examples of the trialkylsilyl group are trimethylsilyl, dimethyl t-butylsilyl, triethylsilyl, t-butyldiphenylsilyl, etc.);

an acetal group (—$CB^5(OB^6)(OB^7)$: wherein $B^5$ is a hydrogen atom or an optionally substituted $C_1$-$C_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amido group, an amino group, or the like.

Examples of substituents which are reactive with the aromatic magnesium reagent but can be introduced via the organozinc reagent include:

an ester group (—$COOB^2$: wherein $B^2$ is a $C_1$-$C_6$ hydrocarbon group (e.g., methyl, ethyl, propyl, isopropyl, n-butyl, sec-butyl, tert-butyl, pentyl, hexyl, phenyl, etc.). Examples of the ester group include methoxycarbonyl, ethoxycarbonyl, 2-methoxyethoxycarbonyl, tert-butoxycarbonyl; a $C_1$-$C_{20}$ alkylcarbonyl (e.g., pivaloyl, etc.); a nitrile group (—CN), and the like.

One or more of the substituents above may be introduced at a substitutable position(s). For example, 1 to 4 substituents may be introduced. Where the number of substituents is 2 or more, the respective substituents may be the same or different.

In the second embodiment of the present invention, R is preferably an optionally substituted primary alkyl group or an optionally substituted secondary alkyl group.

The "optionally substituted primary alkyl group" is preferably 3-N-indolylpropyl, ethoxycarbonylpentyl, octyl, etc.

The "optionally substituted secondary alkyl group" is preferably sec-butyl, cyclohexyl, 4-tert-butylcyclohexyl, cycloheptyl, 2-norbornyl, etc.

In the second embodiment of the present invention, the substituents introduced into the "primary alkyl group" and "secondary alkyl group," which are acceptable as R, are particularly preferably a methoxycarbonyl group, an ethoxycarbonyl group, a tert-butoxycarbonyl group, a cyano group, an alkenyl group, an alkynyl group, a 3-N-indolyl group, an alkyl ether, a silyl ether, a tertiary amino group, a secondary amido group or an acetal.

In the second embodiment of the present invention, X is preferably a halogen atom, more preferably iodine or bromine. While the yield naturally decreases to some extent, X can be chlorine.

In the second embodiment of the present invention, the aromatic magnesium reagent represented by formula (3a) below is used.

$$A\text{-}Mg\text{—}Y^1 \tag{3a}$$

In the formula above, A and $Y^1$ are the same as those given in the first embodiment of the present invention.

In the second embodiment of the present invention, a substituent(s) may be introduced into the "$C_4$-$C_{20}$ aromatic group" or "heteroaromatic group" shown by A. The substituents are preferably those that do not react with the aromatic magnesium reagent.

Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.);

a protected hydroxy group (—$OB^3$: wherein $B^3$ is an alkyl group, an arylalkyl group, an ether-substituted arylalkyl group, an ether-substituted alkyl group, or a silyl group which may be optionally substituted with a $C_1$-$C_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

an acetal group (—$CB^5(OB^6)(OB^7)$: wherein $B^5$ is a hydrogen atom or an optionally substituted $C_1$-$C_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amino group, or the like.

In this case, one or more of the substituents above may be introduced at a substitutable position(s). For example, 1 to 4 substituents may be introduced. Where the number of substituents is 2 or more, the respective substituents may be the same or different.

The substituents cross-bridged with one another may be introduced into 2 or more substitutable positions forming a ring and examples of such substituents include methylenedioxy, ethylenedioxy, tetramethylethylenedioxy, propylenedioxy groups, etc.

In the second embodiment of the present invention, A is preferably an optionally substituted phenyl group or pyridyl group, more preferably phenyl, 2-methylphenyl, 4-methylphenyl, 4-methoxyphenyl or 3,4-(methylenedioxy)phenyl.

In the second embodiment of the present invention, $Y^1$ is preferably iodine, bromine or chlorine.

In the second embodiment of the present invention, the amount of the aromatic magnesium reagent represented by formula (3a) described above is at least 1 mol equivalent, preferably 2 to 4 mol equivalents and most preferably about 3 mol equivalents, based on 1 mol of the compound represented by formula (2) above.

In the second embodiment of the present invention, the magnesium compound represented by formula (4a) below may optionally be used.

$$Z^1\text{—}Mg\text{—}Z^2 \tag{4a}$$

wherein $Z^1$ is a carbanion ligand and $Z^2$ is bromine, iodine or chlorine.

In this case, the amount of the aromatic magnesium reagent represented by formula (3a) described above is at least 1 mol equivalent, preferably 1.5 to 2.5 mol equivalents and most preferably about 2 mol equivalents, based on 1 mol of the compound represented by formula (2) above.

In the second embodiment of the present invention, the zinc compound represented by formula (4b) is used.

$$Z^3\text{—}Zn\text{—}Z^4 \tag{4b}$$

Each of $Z^3$ and $Z^4$, which may be the same or different, independently represents bromine, iodine, chlorine, fluorine or a trifluoromethanesulfonyl group.

In the second embodiment of the present invention, $Z^3$ and $Z^4$ are preferably bromine and chlorine, more preferably chlorine.

In the second embodiment of the present invention, since the zinc compound represented by formula (4b) is employed, nucleophilic and basic properties of substituent A on the zinc are both modest in the organozinc reagent obtained by reacting the said zinc compound with the aromatic magnesium reagent represented by formula (3a) described above. Then, it becomes possible to use as substituent R a substituent having such a functional group (e.g., an ester group, a cyano group, an alkylcarbonyl group, etc.) as reacting with Grignard reagent at room temperature. It is off course possible to modify substituent R into a substituent having an ethoxycarbonyl group also in the first embodiment of the present invention but it invites a somewhat lower yield and tends to cause side reactions. On the other hand, in the second embodiment of the present invention, side reactions occur only with difficulty and the yield is markedly improved. Substituent R can be modified to such a substituent as described above, which is preferred for improving a production efficiency in producing intermediates for medical drugs having a complicated structure by short step synthesis.

Furthermore, in the first embodiment of the present invention, it was required to dropwise add the aromatic magnesium reagent represented by formula (3a) and the diamine compound to a solution containing the compound represented by formula (2) above and the iron catalyst over a long period of time, or to dropwise add the aromatic magnesium reagent represented by formula (3a) to a solution containing the compound represented by formula (2) above, the iron catalyst and the diamine compound over a long period of time. However, the zinc compound represented by formula (4b) above is used in the second embodiment of the present invention so that the dropwise addition over a long period of time is unnecessary when added and operations for the reaction are simplified.

In the second embodiment of the present invention, the amount of the zinc compound represented by formula (4b) described above is at least 1 mol equivalent, preferably in the range of 1.1 to 2 mol equivalents and most preferably about 1.5 mol equivalents, based on 1 mol of the compound represented by formula (2) above.

In the second embodiment of the present invention, the iron catalyst is used. The same description as given in the first embodiment of the present invention applies to the iron catalyst.

The iron catalyst used in the second embodiment of the present invention is preferably an iron (III) halide. In particular, the iron (III) salts such as $FeCl_3$ is preferably employed.

In the second embodiment of the present invention, the amount of the iron catalyst is in the range of 0.001 to 0.5 mol equivalent, preferably 0.01 to 0.1 mol equivalent and most preferably about 0.03 to 0.07 mol equivalent, based on 1 mol of the compound represented by formula (2) above.

In the process for production of the aromatic compound in accordance with the second embodiment of the present invention, the diamine compound is employed. The same description as given in the first embodiment of the present invention applies to the diamine compound.

In the second embodiment of the present invention, the diamine compound is preferably a bidentate ligand, more preferably an ethylenediamine which may optionally have a substituent such as N,N,N',N'-tetramethylethylenediamine (TMEDA), etc.

In the second embodiment of the present invention, the amount of the diamine compound is in the range of 0.5 to 10 mol equivalents, preferably 1 to 3 mol equivalents and most preferably 1 to 2 mol equivalents, based on 1 mol of the compound represented by formula (2) above.

In the second embodiment of the present invention, typically the compound represented by formula (2) above and the iron catalyst described above are added to a solution containing the aromatic magnesium reagent represented by formula (3a) described above, the zinc compound represented by formula (4b) described above and the diamine compound described above, and the mixture is stirred.

In the second embodiment of the present invention, a complex of the zinc compound represented by formula (4b) described above and the diamine compound can also be used, instead of using these compounds separately.

In the second embodiment of the present invention, the reaction is carried out preferably in a temperature range of 0° C. to 100° C., more preferably in a temperature range of 40° C. to 60° C. The pressure is preferably under normal pressure.

In the second embodiment of the present invention, the solvent is preferably a solvent which can dissolve the compound represented by formula (2) above. An aliphatic or aromatic organic solvent is used as the solvent. For example, an ethereal solvent such as tetrahydrofuran, diethyl ether, etc.; an aromatic hydrocarbon such as toluene, etc. is used.

According to the third embodiment of the present invention, there is provided a process for production of the aromatic compound represented by formula (1) below, which comprises the step of reacting the aromatic lithium reagent represented by formula (3c) below with the zinc compound represented by formula (4b) below, in the presence of the diamine compound, and then reacting with a Lewis acid metal compound containing at least one metal selected from the group consisting of magnesium, titanium, zirconium, hafnium, gallium and aluminum to give the reaction mixture; and, the step of reacting the reaction mixture with the compound represented by formula (2) below in the presence of the iron catalyst.

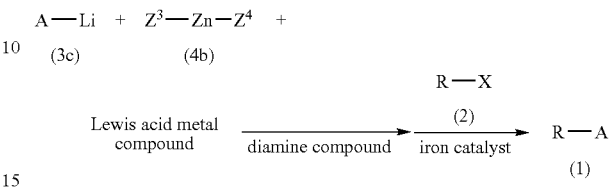

wherein R, X, $Z^3$, $Z^4$ and A have the same significance as described above.

In the third embodiment of the present invention, the compound represented by formula (2) below is employed.

$$R—X \qquad (2)$$

In the formula above, R and X are the same as those given in the first embodiment of the present invention.

In the third embodiment of the present invention, a substituent(s) may be introduced into the "hydrocarbon group" or "$C_3$-$C_{10}$ saturated ring group or unsaturated ring group" shown by R, or into the "$C_1$-$C_{10}$ hydrocarbon group" and "$C_1$-$C_{10}$ alkoxycarbonyl group" shown by B when R is the "$C_3$-$C_{10}$ saturated ring group or unsaturated ring group, which ring may optionally be intervened by the group represented by formula —N(B)—." The substituent(s) are preferably those that do not react with the organozinc reagent obtained by reacting the aromatic lithium reagent represented by formula (3c) described above with the zinc compound represented by formula (4b) described above and then reacting with the Lewis acid metal compound described above.

Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.);

a $C_2$-$C_{20}$ alkenyl-$C_1$-$C_{20}$ alkyl-$C_1$-$C_{20}$ alkoxy (e.g., 1-vinyl-1-methylethoxy, etc.);

a $C_6$-$C_{20}$ aryl-$C_1$-$C_{20}$ alkyloxycarbonyl (e.g., benzyloxycarbonyl, etc.);

a $C_1$-$C_{20}$ alkyl-carbonyloxy (e.g., acetoxy, propanoyloxy, pivaloyloxy, etc.);

a protected hydroxy group (—$OB^3$: wherein $B^3$ is an alkyl group, an arylalkyl group, an ether-substituted arylalkyl group, an ether-substituted alkyl group, or a silyl group which may be optionally substituted with a $C_1$-$C_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

a trialkylsilyl group (—$B^4$: wherein $B^4$ is an optionally substituted silyl group, which may optionally be substituted with a $C_1$-$C_6$ hydrocarbon group (e.g., methyl, ethyl, propyl, isopropyl, n-butyl, sec-butyl, tert-butyl, pentyl, hexyl, phenyl, etc.), etc. Examples of the trialkylsilyl group are trimethylsilyl, dimethyl t-butylsilyl, triethylsilyl, t-butyldiphenylsilyl, etc.);

an acetal group (—$CB^5(OB^6)(OB^7)$): wherein $B^5$ is a hydrogen atom or an optionally substituted $C_1$-$C_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amido group, an amino group, or the like.

Examples of substituents which are reactive with the aromatic lithium reagent but can be introduced via the organozinc reagent include:

an ester group (—$COOB^2$: wherein $B^2$ is a $C_1$-$C_6$ hydrocarbon group (e.g., methyl, ethyl, propyl, isopropyl, n-butyl, sec-butyl, tert-butyl, pentyl, hexyl, phenyl, etc.). Examples of the ester group include methoxycarbonyl, ethoxycarbonyl, 2-methoxyethoxycarbonyl, tert-butoxycarbonyl; a $C_1$-$C_{20}$ alkylcarbonyl (e.g., pivaloyl, etc.); a nitrile group (—CN), etc.

One or more of the substituents above may be introduced at a substitutable position(s). For example, 1 to 4 substituents may be introduced. Where the number of substituents is 2 or more, the respective substituents may be the same or different.

In the third embodiment of the present invention, R is preferably an optionally substituted primary alkyl group or an optionally substituted secondary alkyl group.

The "optionally substituted primary alkyl group" is preferably 3-N-indolylpropyl, ethoxycarbonylpentyl, octyl, etc.

The "optionally substituted secondary alkyl group" is preferably sec-butyl, cyclohexyl, 4-tert-butylcyclohexyl, cycloheptyl, 2-norbornyl, etc.

In the third embodiment of the present invention, the substituents introduced into the "primary alkyl group" and "secondary alkyl group," which are acceptable as R, are particularly preferably a methoxycarbonyl group, an ethoxycarbonyl group, a tert-butoxycarbonyl group, a cyano group, an alkenyl group, an alkynyl group, a 3-N-indolyl group, an alkyl ether, a silyl ether or an acetal.

In the third embodiment of the present invention, X is preferably a halogen atom, more preferably iodine or bromine. While the yield naturally decreases to some extent, X can be chlorine.

In the third embodiment of the present invention, the aromatic lithium reagent represented by formula (3c) below is used.

$$A\text{-}Li \quad (3c)$$

In the formula above, A is the same as the description given in the first embodiment of the present invention.

In the third embodiment of the present invention, a substituent(s) may be introduced into the "$C_4$-$C_{20}$ aromatic group" or "heteroaromatic group" shown by A. The substituent(s) are preferably those that do not react with the organic lithium reagent.

Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.);

a protected hydroxy group (—$OB^3$: wherein $B^3$ is an alkyl group, an arylalkyl group, an ether-substituted arylalkyl group, an ether-substituted alkyl group, or a silyl group which may be optionally substituted with a $C_1$-$C_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

an acetal group (—$CB^5(OB^6)(OB^7)$): wherein $B^5$ is a hydrogen atom or an optionally substituted $C_1$-$C_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amino group, etc.

In this case, one or more of the substituents above may be introduced at a substitutable position(s). For example, 1 to 4 substituents may be introduced. Where the number of substituents is 2 or more, the respective substituents may be the same or different.

When a halogen atom is introduced to substituent A, the operation of preparing the aromatic lithium reagent at a temperature of −78° C. or lower is required to prevent side reactions due to the formation of benzynes. And when the aromatic lithium reagent is used, the operation of mixing with the zinc compound at a low temperature to prepare the organozinc reagent is also required.

The substituents cross-bridged with one another may be introduced into 2 or more substitutable positions forming a ring and examples of such substituents include methylenedioxy, ethylenedioxy, tetramethylethylenedioxy, propylenedioxy groups, etc.

In the third embodiment of the present invention, A is preferably an aromatic group such as an optionally substituted phenyl group, a naphthyl group, etc., or a heteroaromatic group such as a pyridyl group, a benzofuryl group, etc., more preferably phenyl, 2-methylphenyl, 4-methylphenyl, 4-methoxyphenyl, 3,4-(methylenedioxy)phenyl or 2-pyridyl.

In the third embodiment of the present invention, the amount of the aromatic lithium reagent represented by formula (3c) described above is at least 1 mol equivalent, preferably in the range of 1.1 to 3 mol equivalents and most preferably about 2 mol equivalents, based on 1 mol of the compound represented by formula (2) above.

In the third embodiment of the present invention, the Lewis acid metal compound containing at least one metal selected from the group consisting of magnesium, titanium, zirconium, hafnium, gallium and aluminum is employed.

As the Lewis acid metal compound used in the third embodiment of the present invention, for example, the metal compound represented by formula (4c) below is used.

$$M(Z^1)_n \qquad (4c)$$

In the formula above, M is magnesium, titanium, zirconium, hafnium, gallium or aluminum.

Each of $Z^1$, which may be the same or different, independently represents bromine, iodine, chlorine or a carbanion ligand; and n is an integer of 2 to 4.

In the third embodiment of the present invention, when M is magnesium, preferably n is 2 wherein one $Z^1$ is a trimethylsilylmethyl group and another $Z^1$ is bromine or chlorine, more preferably one $Z^1$ is a trimethylsilylmethyl group and another $Z^1$ is chlorine.

Examples of other metal compounds also used in the third embodiment of the present invention include salts of at least one metal selected from the group consisting of magnesium, titanium, zirconium, hafnium, gallium and aluminum with an inorganic acid such as hydrochloric acid, sulfuric acid, etc. Preferred are metal halides. Particularly preferred are $MgBr_2$, $TiCl_4$, $ZrCl_4$, $HfCl_4$, $Ga_2Cl_4$ and $AlCl_3$.

In the third embodiment of the present invention, the zinc compound represented by formula (4b) below is employed.

$$Z^3\text{---}Zn\text{---}Z^4 \qquad (4b)$$

In the formula above, $Z^3$ and $Z^4$ are the same as those given in the second embodiment of the present invention.

In the third embodiment of the present invention, $Z^3$ and $Z^4$ are preferably bromine or chlorine, more preferably chlorine.

In the third embodiment of the present invention, since the aromatic lithium reagent represented by formula (3c) described above and the zinc compound represented by formula (4b) described above are employed, nucleophilic and basic properties of the organozinc reagent produced from both are modest. Then, it becomes possible to use as substituent R a substituent having such a functional group (e.g., an ester group, a cyano group, an alkylcarbonyl group, etc.) as reacting with aromatic lithium reagent at room temperature. It is off course possible to modify substituent R into a substituent having an ethoxycarbonyl group also in the first embodiment of the present invention but it invites a somewhat lower yield and tends to cause side reactions. On the other hand, in the third embodiment of the present invention, side reactions occur only with difficulty and the yield is markedly improved, as in the second embodiment of the present invention.

In addition, it becomes possible to prepare the aromatic lithium reagent (3c) from various heterocyclic compounds. Thus, a wide variety of aromatic rings A can be introduced through coupling. Substituent R and substituent A can be modified to such substituents, which is preferred for improving a process efficiency in producing intermediates for medical drugs, and agricultural chemicals and organic light-emitting materials, having a more complicated structure by short step synthesis.

In the third embodiment of the present invention, the amount of the Lewis acid metal compound is at least 1 mol equivalent, preferably in the range of 1 to 2 mol equivalents and most preferably about 1.0 mol equivalent, based on 1 mol of the compound represented by formula (3c) above.

In the third embodiment of the present invention, the amount of the zinc compound represented by formula (4b) described above is at least 1 mol equivalent, preferably in the range of 1.1 to 2 mol equivalents and most preferably about 1.5 mol equivalents, based on 1 mol of the compound represented by formula (2) above.

In the third embodiment of the present invention, where the organozinc reagent [$A_2Zn$] is prepared by mixing the aromatic lithium reagent (3c) and the zinc compound (4b) in a molar ratio of 2:1, the Lewis acid metal compound may be an inorganic salt (e.g., $MgBr_2$, $TiCl_4$, $ZrCl_4$, $HfCl_4$, $Ga_2Cl_4$, $AlCl_3$) and the amount used may be at most 1 mol equivalent to zinc, or can be reduced to 0.1 mol equivalent.

Furthermore, in the third embodiment of the present invention, where the organozinc reagent [A-Zn—$Z^3$ or A-Zn—$Z^4$] is prepared by mixing the aromatic lithium reagent (3c) and the zinc compound (4b) in a molar ratio of 1:1, the Lewis acid metal compound is the magnesium compound (4a), $Z^1$ is a trimethylsilylmethyl group and about 1 mol equivalent should be used for the zinc.

In the third embodiment of the present invention, the iron catalyst is employed. The same description as given in the first embodiment of the present invention applies to the iron catalyst.

The iron catalyst used in the third embodiment of the present invention is preferably an iron (III) halide. In particular, iron (III) salts such as $FeCl_3$ are preferably used.

In the third embodiment of the present invention, the amount of the iron catalyst is 0.001 to 0.5 mol equivalent, preferably in the range of 0.01 to 0.1 mol equivalent and most preferably about 0.03 to 0.07, based on 1 mol of the compound represented by formula (2) above.

In the process for production of the aromatic compound in accordance with the third embodiment of the present invention, the diamine compound is employed. The same description as given in the first embodiment of the present invention applies to the diamine compound.

In the third embodiment of the present invention, the diamine compound is preferably a bidentate ligand, more preferably an ethylenediamine which may optionally have a substituent such as N,N,N',N'-tetramethylethylenediamine (TMEDA), etc.

In the third embodiment of the present invention, the amount of the diamine compound is in the range of 0.5 to 10 mol equivalents, preferably 1 to 3 mol equivalents and most preferably about 1 to 2 mol equivalents, based on 1 mol of the compound represented by formula (2) described above.

In the third embodiment of the present invention, typically the compound represented by formula (2) described above and the iron catalyst described above are added to a solution containing the aromatic lithium reagent represented by formula (3a) described above, the magnesium compound represented by formula (4b) described above, the zinc compound represented by formula (4b) described above and the diamine compound described above, and the mixture is stirred.

In the third embodiment of the present invention, a complex of the zinc compound represented by formula (4b) described above and the diamine compound can also be used, instead of using these compounds separately.

In the third embodiment of the present invention, the reaction is carried out preferably in a temperature range of 0° C. to 100° C., more preferably in a temperature range of 40° C. to 60° C. The pressure is preferably under normal pressure.

In the third embodiment of the present invention, the solvent is preferably a solvent which can dissolve the compound represented by formula (2) above. An aliphatic or aromatic organic solvent is used as the solvent. For example, an ethereal solvent such as tetrahydrofuran, diethyl ether, etc.; an aromatic hydrocarbon such as toluene, etc. is used. Hydrocarbons such as hexane originating from the aromatic lithium reagent, etc. may also be mixed.

According to the fourth embodiment of the present invention, there is provided a process for production of the aromatic compound represented by formula (1) below, which comprise the step of reacting the aromatic zinc reagent represented by formula (3b) described below with the magnesium compound represented by formula (4a) in the presence of the diamine compound to give the reaction mixture; and, the step of reacting the reaction mixture above with the compound represented by formula (2) below in the presence of the iron catalyst.

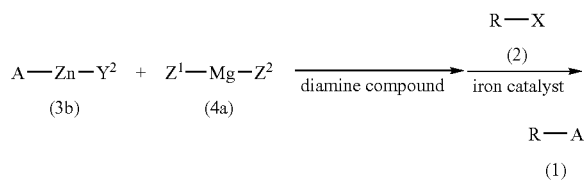

wherein R, X, $Z^1$, $Z^2$ and A have the same significance as described above.

In the fourth embodiment of the present invention, the compound represented by formula (2) below is used.

$$R—X \quad (2)$$

In the formula above, R and X are the same as those given in the first embodiment of the present invention.

In the fourth embodiment of the present invention, a substituent(s) may be introduced into the "hydrocarbon group" or "$C_3$-$C_{10}$ saturated ring group or unsaturated ring group" shown by R, or into the "$C_1$-$C_{10}$ hydrocarbon group" and "$C_1$-$C_{10}$ alkoxycarbonyl group" shown by B when R is the "$C_3$-$C_{10}$ saturated ring group or unsaturated ring group, which ring may optionally be intervened by the group represented by formula —N(B)—." The substituent(s) are preferably those that do not react with the organozinc reagent obtained by reacting the aromatic zinc reagent represented by formula (3b) described above with the magnesium compound represented by formula (4a) described above.

Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.);

an ester group (—COO$B^2$: wherein $B^2$ is a $C_1$-$C_6$ hydrocarbon group (e.g., methyl, ethyl, propyl, isopropyl, n-butyl, sec-butyl, tert-butyl, pentyl, hexyl, phenyl, etc.). Examples of the ester group include methoxycarbonyl, ethoxycarbonyl, 2-methoxyethoxycarbonyl, tert-butoxycarbonyl;

a $C_1$-$C_{20}$ alkylcarbonyl (e.g., pivaloyl, etc.);

a nitrile group (—CN);

a $C_2$-$C_{20}$ alkenyl-$C_1$-$C_{20}$ alkyl-$C_1$-$C_{20}$ alkoxy (e.g., 1-vinyl-1-methylethoxy, etc.);

a $C_6$-$C_{20}$ aryl-$C_1$-$C_{20}$ alkyloxycarbonyl (e.g., benzyloxycarbonyl, etc.);

a $C_1$-$C_{20}$ alkyl-carbonyloxy (e.g., acetoxy, propanoyloxy, pivaloyloxy, etc.);

a protected hydroxy group (—O$B^3$: wherein $B^3$ is an alkyl group, an arylalkyl group, an ether-substituted arylalkyl group, an ether-substituted alkyl group, or a silyl group which may be optionally substituted with a $C_1$-$C_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

a trialkylsilyl group (—$B^4$: wherein $B^4$ is an optionally substituted silyl group, which may optionally be substituted with a $C_1$-$C_6$ hydrocarbon group (e.g., methyl, ethyl, propyl, isopropyl, n-butyl, sec-butyl, tert-butyl, pentyl, hexyl, phenyl, etc.), etc. Examples of the trialkylsilyl group are trimethylsilyl, dimethyl tert-butylsilyl, triethylsilyl, tert-butyldiphenylsilyl, etc.);

an acetal group (—C$B^5$(O$B^6$)(O$B^7$): wherein $B^5$ is a hydrogen atom or an optionally substituted $C_1$-$C_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amido group, an amino group, etc.

One or more of the substituents above may be introduced at a substitutable position(s). For example, 1 to 4 substituents may be introduced. Where the number of substituents is 2 or more, the respective substituents may be the same or different.

In the fourth embodiment of the present invention, R is preferably an optionally substituted primary alkyl group or an optionally substituted secondary alkyl group.

The "optionally substituted primary alkyl group" is preferably 3-N-indolylpropyl, ethoxycarbonylpentyl, octyl, etc.

The "optionally substituted secondary alkyl group" is preferably sec-butyl, cyclohexyl, 4-tert-butylcyclohexyl, cycloheptyl, 2-norbornyl, etc.

In the fourth embodiment of the present invention, the substituents introduced into the "primary alkyl group" and "secondary alkyl group," which are acceptable as R, are particularly preferably a methoxycarbonyl group, an ethoxycarbonyl group, a tert-butoxycarbonyl group, a cyano group, an alkenyl group, an alkynyl group, a 3-N-indolyl group, an alkyl ether, a silyl ether or an acetal.

In the fourth embodiment of the present invention, X is preferably a halogen atom, more preferably iodine or bromine. While the yield naturally decreases to some extent, X can be chlorine.

In the fourth embodiment of the present invention, the aromatic zinc regent represented by formula (3b) below is used.

$$A\text{-}Zn—Y^2 \quad (3b)$$

In the formula above, A is the same as the description given in the first embodiment of the present invention.

In the fourth embodiment of the present invention, a substituent(s) may be introduced into the "$C_4$-$C_{20}$ aromatic group" and "heteroaromatic group" shown by A.

Examples of the substituents include:

an optionally substituted $C_1$-$C_{10}$ alkyl group (e.g., methyl, ethyl, propyl, butyl, trifluoromethyl, etc.);

a $C_2$-$C_{10}$ alkenyl group (e.g., vinyl, allyl, propenyl, isopropenyl, 2-methyl-1-propenyl, 2-methylallyl, 2-butenyl, etc.);

a $C_2$-$C_{20}$ alkynyl group (e.g., ethynyl, propynyl, butynyl, etc.);

an ester group (—COO$B^2$: wherein $B^2$ is a $C_1$-$C_6$ hydrocarbon group (e.g., methyl, ethyl, propyl, isopropyl, n-butyl, sec-butyl, tert-butyl, pentyl, hexyl, phenyl, etc.). Examples of the ester group include methoxycarbonyl, ethoxycarbonyl, 2-methoxyethoxycarbonyl, tert-butoxycarbonyl, etc.);

a nitrile group (—CN);

a $C_1$-$C_{20}$ alkylcarbonyl (e.g., pivaloyl, etc.);

a protected hydroxy group (—$OB^3$: wherein $B^3$ is an alkyl group, an arylalkyl group, an ether-substituted arylalkyl group, an ether-substituted alkyl group, or a silyl group which may be optionally substituted with a $C_1$-$C_6$ hydrocarbon group (e.g., methyl, ethyl, propyl, isopropyl, n-butyl, sec-butyl, tert-butyl, pentyl, hexyl, phenyl, etc.) or the like. Examples of the protected hydroxy group include methoxy group, benzyloxy group, p-methoxybenzyloxy group, methoxymethyl group, ethoxyethyl group, trimethylsiloxy, dimethyl tert-butylsiloxy, triethylsiloxy, tert-butyldiphenylsiloxy, etc.);

an acetal group (—$CB^5(OB^6)(OB^7)$: wherein $B^5$ is a hydrogen atom or an optionally substituted $C_1$-$C_6$ alkyl group; each of $B^6$ and $B^7$, which may be the same or different, independently represents an optionally substituted $C_1$-$C_6$ hydrocarbon group (e.g., methyl, ethyl, propyl, isopropyl, n-butyl, sec-butyl, tert-butyl, pentyl, hexyl, phenyl, etc.) and they may be cross-bridged with one another. Examples of $B^6$ and $B^7$ are a methyl group, an ethyl group, etc. and when they are cross-bridged with one another, examples include an ethylene group, a trimethylene group, etc.); a N-indolyl; a $C_1$-$C_{10}$ alkoxy group (e.g., methoxy, ethoxy, propoxy, butoxy, etc.); a $C_6$-$C_{10}$ aryloxy group (e.g., phenyloxy, naphthyloxy, biphenyloxy, etc.); a halogen atom (e.g., fluorine, chlorine, bromine, iodine); an amino group, etc.

In this case, one or more of the substituents above may be introduced at a substitutable position(s). For example, 1 to 4 substituents may be introduced. Where the number of substituents is 2 or more, the respective substituents may be the same or different.

The substituents cross-bridged with one another may be introduced into 2 or more substitutable positions forming a ring and examples of such substituents include methylenedioxy, ethylenedioxy, tetramethylethylenedioxy, propylenedioxy groups, etc.

In the fourth embodiment of the present invention, A is preferably an optionally substituted phenyl or a variety of heteroaromatic groups such as pyridyl group, more preferably phenyl, 2-methylphenyl, 4-methylphenyl, 4-methoxyphenyl, 3,4-(methylenedioxy)phenyl, 3-(ethoxycarbonyl) phenyl, 4-cyanophenyl and 2-pyridyl.

In the formula (3b) above, $Y^2$ is bromine, iodine or chlorine.

In the fourth embodiment of the present invention, the amount of the aromatic zinc reagent represented by formula (3b) described above is at least 1 mol equivalent, preferably 1.1 to 2 mol equivalents and most preferably about 1.5 mol equivalents, based on 1 mol of the compound represented by formula (2) above.

In the fourth embodiment of the present invention, the magnesium compound represented by formula (4a) is employed.

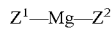

$Z^1$—Mg—$Z^2$                           (4a)

In the formula above, $Z^1$ is a carbanion ligand and $Z^2$ is bromine, iodine or chlorine.

In the fourth embodiment of the present invention, more preferably $Z^1$ is the same aromatic group as in substituent A or a trimethylsilylmethyl group, and $Z^2$ is preferably bromine or chlorine, more preferably bromine.

In the fourth embodiment of the present invention, since the aromatic zinc regent represented by formula (3b) is used, substituents having a wide variety of functional groups can be used as substituents R and A. Such functional groups include an ester group, a cyano group, an alkylcarbonyl group, etc., which are unstable to the aromatic magnesium reagent or the aromatic lithium reagent.

In the fourth embodiment of the present invention, the amount of the magnesium compound represented by formula (4a) described above is at least 1 mol equivalent, preferably 1.1 to 2 mol equivalents and most preferably about 1.5 mol equivalents, based on 1 mol of the compound represented by formula (2) above.

In the fourth embodiment of the present invention, the iron catalyst is employed. The same description as given in the first embodiment of the present invention applies to the iron catalyst.

The iron catalyst used in the fourth embodiment of the present invention is preferably an iron (III) halide. In particular, iron (III) salts such as $FeCl_3$ are preferably used.

In the fourth embodiment of the present invention, the amount of the iron catalyst is in the range of 0.001 to 0.5 mol equivalent, preferably 0.01 to 0.1 mol equivalent and most preferably 0.03 to 0.07 mol equivalent, based on 1 mol of the compound represented by formula (2) above.

In the process for production of the aromatic compound in accordance with the fourth embodiment of the present invention, the diamine compound is employed. The same description as given in the first embodiment of the present invention applies to the diamine compound.

In the fourth embodiment of the present invention, the diamine compound is preferably a bidentate ligand, more preferably an ethylenediamine which may optionally have a substituent such as N,N,N',N'-tetramethylethylenediamine (TMEDA), etc.

In the fourth embodiment of the present invention, the amount of the diamine compound is in the range of 0.5 to 10 mol equivalent, preferably 1 to 3 mol equivalents and most preferably 1 to 2 mol equivalents, based on 1 mol of the compound represented by formula (2) above.

In the fourth embodiment of the present invention, typically a mixture of the aromatic zinc reagent represented by formula (3b) described above, the magnesium compound represented by formula (4b) above and the diamine compound is prepared in the presence of the diamine compound. Then, the compound represented by formula (2) described above and the iron catalyst are added to the above solution, and the mixture is stirred.

In the fourth embodiment of the present invention, the reaction is carried out preferably in a temperature range of 0° C. to 100° C., more preferably in a temperature range of 40° C. to 60° C. The pressure is preferably under normal pressure.

In the fourth embodiment of the present invention, the solvent is preferably a solvent which can dissolve the compound represented by formula (2) above. An aliphatic or aromatic organic solvent is used as the solvent. For example, an ethereal solvent such as tetrahydrofuran, diethyl ether, etc.; an aromatic hydrocarbon such as toluene, etc. is used.

EXAMPLES

Hereinafter, the present invention will be described with reference to EXAMPLES but is not deemed to be limited to EXAMPLES below.

All the reactions dealing with the compounds sensitive to air or moisture were performed in dried reactors under argon or nitrogen atmosphere. Air and moisture-sensitive liquids and solutions were transferred via syringe or a stainless steel cannula. Analytical thin-layer chromatography was performed using glass plates precoated with 25-μm 230-400 mesh silica gel impregnated with a fluorescent indicator (254 nm). Thin layer chromatography plates were visualized by exposure to ultraviolet light (UV) and/or by immersion in p-anisaldehyde followed by heating on a hot plate. Organic solutions were concentrated by operating a rotary evaporator equipped with a diaphragm pump at ca. 15 torr. Flash column chromatography was performed on Kanto Silica Gel 60 (spherical, neutral, 140-325 mesh), as described in Still, W. C.; Klahn, M.; Mitra, A. *J. Org. Chem.* 1978, 43, 2923-2924.

Materials: Commercial reagents were purchased from Tokyo Kasei Industry Co., Ltd., Aldrich Inc., and other suppliers and were used either distilled or recrystallized. Anhydrous tetrahydrofuran (THF), purchased from Kanto Chemical Co., Inc., was distilled from benzophenone ketyl at 760 Torr under an argon atmosphere and immediately provided for use. The water content of the solvent was confirmed with a Karl-Fischer moisture titrator to be less than 20 ppm. $FeCl_3$, purchased from Kanto Chemical Co., Inc., was dehydrated with thionyl chloride to completely remove an excess of thionyl chloride under reduced pressure, and anhydrous $FeCl_3$ obtained was subsequently stored under an argon atmosphere. By storing at room temperature for several days, 0.1 M THF solution of $FeCl_3$ forms polyether compounds to deteriorate its catalytic activity. Thus, the THF solution was provided for use immediately after preparation.

Instrumentation: Proton nuclear magnetic resonance ($^1H$ NMR) and carbon nuclear magnetic resonance ($^{13}C$ NMR) were recorded with JEOL AL-400 (400 MHz), JEOL ECX-400 (400 MHz) or JEOL ECA-500 (500 MHz) NMR spectrometer. Chemical shifts for hydrogen atoms were reported per million (ppm, δ scale) downfield from tetramethylsilane and were referenced to residual proton in the NMR solvent ($CDCl_3$: δ 7.26). Carbon nuclear magnetic resonance spectra ($^{13}C$ NMR) were recorded at 125 or 100 MHz. Chemical shifts for carbons were reported per million (ppm, δ scale) downfield from tetramethylsilane and were referenced to the carbon resonance of the NMR solvent ($CDCl_3$: δ 77.0). The data are presented as follows: chemical shift, multiplicity (s=singlet, d=doublet, t=triplet, q=quartet, m=multiplet and/or multiplet resonances, br=broad), coupling constant (Hertz: Hz), and integration.

Gas chromatographic (GC) analyses were conducted on Shimadzu GC-14B instruments equipped with an FID detector and a capillary column, HR-1 (25 m×0.25 mm i.d., 0.25 μm film), CYCLOSILB (Agilent Technologies, Inc., 30 m×0.25 mm i.d., 0.25 μm film) or CHIRALDEX G-TA (ASTEC, Inc., 20 m×0.25 mm i.d., 0.125 μm film). IR spectra were recorded on a React IR 1000 Reaction Analysis System equipped with DuraSample IR (ASI Applied System) and reported in $cm^{-1}$. Mass spectra were conducted on JEOL GC-mate II.

Example 1

Following the details given below, effects of the additives on selectivity and yield of the products were examined.

First, 0.96-M THF solution of phenyl magnesium bromide (1.25 mL, 1.2 mmol), various additives (1.2 mmol) shown in TABLE 1 below and bromocycloheptane (177 mg, 1.0 mmol) (shown by "1" in TABLE 1 below) were charged in a 50-mL glass tube equipped with a magnetic stirrer and cooled to −78° C. At this temperature, 0.1-M THF solution of $FeCl_3$ (0.5 mL, 5 mol %) was added to the mixture. The resulting solution was put in an ice bath and stirred at 0° C. for 30 minutes. Saturated aqueous solution (0.5 mL) of $NH_4Cl$ was added to terminate the reaction. After conventional treatments, the amount of bromocyclopentane consumed and the yields of compounds produced (shown by "2," "3" and "4" in TABLE 1 below) and biphenyl were determined by gas chromatography (internal standard (n-decane, 71 mg, 0.5 mmol)). The results are shown in TABLE 1.

TABLE 1

| entry | additive | % yield | | | | |
|---|---|---|---|---|---|---|
| | | 2 | 3 | 4 | 1 | Ph—Ph |
| 1 | none | 5 | 79 | 0 | 4 | 6 |
| 2 | $Et_3N$ (1.2 equiv) | 3 | 78 | 0 | 11 | 5 |
| 3 | N-methylmorpholine (1.2 equiv) | 8 | 72 | 0 | 4 | 5 |
| 4 | DABCO (1.2 equiv) | 20 | 2 | 0 | 75 | 3 |
| 5 | TMEDA (1.2 equiv) | 71 | 19 | 3 | trace | 10 |
| 6 | $Et_2N$‑‑‑$NEt_2$ (1.2 equiv) | 23 | 48 | 1 | 11 | 9 |
| 7 | NMP (1.2 equiv) | 15 | 3 | trace | 79 | 4 |
| 8 | $PPh_3$ (0.1 equiv) | 6 | 70 | trace | 6 | 7 |
| 9 | dppe (0.05 equiv) | 4 | 8 | 0 | 81 | 8 |

In TABLE 1, "DABCO," "NMP" and "dppe" are short for 1,4-diazabicyclo[2.2.2]octane, 1-methyl-2-pyrrolidinone and 1,2-bisdiphenylphosphinoethane, respectively.

It is understood from TABLE 1 that when N,N,N',N'-tetramethylethylenediamine (TMEDA) is used as an additive, alkylated aromatic compounds can be produced most efficiently.

Example 2

Next, various iron compounds available as catalyst precursors were selected.

Specifically, the procedures were conducted in a manner similar to EXAMPLE 1, except that various iron catalysts shown in TABLE 2 below were used as the iron catalyst and TMEDA was used as the additive. The results are shown in TABLE 2.

TABLE 2

Iron catalyst - coupling reaction using various catalyst precursors

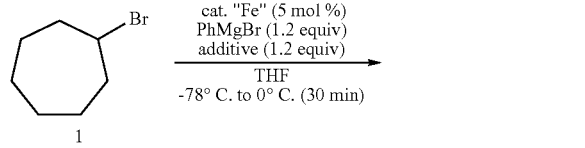

| entry | cat. Fe | 2 | 3 | 4 | 1 | Ph—Ph |
|---|---|---|---|---|---|---|
| 10 | FeCl$_3$ | 71 | 19 | 3 | trace | 10 |
| 11 | FeF$_3$ | 0 | 0 | 0 | 97 | 2 |
| 12 | Fe(acac)$_3$ | 14 | 6 | 1 | 71 | 10 |
| 13 | FeCl$_2$ | 32 | 10 | 1 | 56 | 10 |
| 14 | Fe(CO)$_5$ | trace | trace | 0 | 95 | 5 |

In TABLE 2, "Fe(acac)$_3$" is short for iron (III) acetylacetonate complex.

It is understood from TABLE 2 that when FeCl$_3$ was used, alkylated aromatic compounds can be produced most efficiently.

Example 3

Next, using various alkyl halides and Grignard reagent, it was attempted to introduce a wide variety of alkyl groups into aromatic rings.

Specifically, the procedures were conducted in a manner similar to EXAMPLE 1, except that FeCl$_3$ was used as the iron catalyst, TMEDA was used as the additive and other reagents were used as given in TABLE 3.

In the table, the reaction was carried out under the slow addition conditions of a 1-mmol scale, unless otherwise indicated.

In the table, the reaction was carried out at the temperature of 0° C. in Entry Nos. 15-17, 25, 28 and 31-35 and at the temperature of 25° C. in Entry Nos. 18-24, 26 and 29, unless otherwise indicated.

In the table, Grignard reagent was used in an amount of 1.2 equivalents, unless otherwise indicated.

In the table, the yield was determined by gas chromatography using an internal standard or $^1$H NMR, unless otherwise indicated. The results are shown in TABLE 3.

TABLE 3

| entry | alkyl halide | ArMgBr | product | % yield |
|---|---|---|---|---|
| 15 | cycloheptyl-Br | Ar = Ph | cycloheptyl-Ph | 96 (90%)$^{e,f}$ |
| 16 | cyclohexyl-X | Ar = Ph | | 99 (X = I) |
| 17 | | | | 99 (X = Br)$^e$ |
| 18 | | | | 99 (X = Cl)$^g$ |
| 19 | cyclohexyl-Br | Ar = 4-MeOC$_6$H$_4$ | cyclohexyl-Ar | 99$^e$ |
| 20 | | Ar = 4-MeC$_6$H$_4$ | | 98 (96)$^e$ |
| 21 | | Ar = 4-CF$_3$C$_6$H$_4$ | | 67$^{e,h}$ |
| 22$^i$ | | Ar = 2-naphtyl | | 96 |
| 23$^i$ | | Ar = 1-naphtyl | | 97$^j$ |
| 24 | | Ar = 2-MeC$_6$H$_4$ | | 99 (98)$^e$ |
| 25 | iBu-X | Ar = Ph | iBu-Ph | 95 (X = I) |
| 26 | | | | 94 (X = Br) |
| 27 | | | | 84 (X = Cl)$^{g,k}$ |
| 28 | n-C$_8$H$_{17}$-X | Ar = Ph | n-C$_8$H$_{17}$-Ph | 97 (X = I) |
| 29 | | | | 91 (X = Br) |
| 30 | | | | 45 (X = Cl)$^{g,k}$ |
| 31 | norbornyl-Br | Ar = 4-MeOC$_6$H$_4$ | norbornyl-Ar (exo:endo = 95:5) | 91 |
| 32$^i$ | t-Bu-cyclohexyl-Br | Ar = 4-MeOC$_6$H$_4$ | t-Bu-cyclohexyl-Ar (trans:cis = 96:4) | 96$^e$ |
| 33$^i$ | t-Bu-cyclohexyl-Br | Ar = 4-MeOC$_6$H$_4$ | t-Bu-cyclohexyl-Ar | 98 |

TABLE 3-continued

| entry | alkyl halide | ArMgBr | product | % yield |
|---|---|---|---|---|
| | | | (trans:cis = 96:4) | |
| 34 | EtO-C(=O)-(CH$_2$)$_5$-I | Ar = 4-MeOC$_6$H$_4$ | EtO-C(=O)-(CH$_2$)$_5$-Ar | 88[e] |
| 35 | indole-N-(CH$_2$)$_3$-I | Ar = 4-MeOC$_6$H$_4$ | indole-N-(CH$_2$)$_3$-Ar | 87[e] |

[e]Isolated yield
[f]Run in a larger 50-mmol scale
[g]Grignard reagent was used in an amount of 1.5 equivalents.
[h]Grignard reagent was used in an amount of 2.0 equivalents.
[i]Grignard reagent was added to the mixture of bromochlorohexane, FeCl$_3$ and TMEDA.
[j]Grignard reagent was used in an amount of 1.8 equivalents.
[k]The reaction temperature was set at 40°.
[l]0.5-mmol scale The process for production, measurements, etc and so on of several runs in TABLE 3 are specifically described below.

Entry No. 15

Cycloheptylbenzene

In a 50-mmol Scale

A mixture of PhMgBr (72 mL of 0.93-M THF solution, 67 mmol) and TMEDA (7.78 g, 67 mmol) was added to a mixture of bromocycloheptane (8.85 g, 50 mmol), FeCl$_3$ (25 mL of 0.1-M THF solution, 5 mol %) at 0° C. in such a rate as keeping the reaction mixture in its pale yellow solution (1.36 mL/min. in the case of this run), using an injection pump. After completion of the addition of PhMgBr/TMEDA, the reaction mixture was stirred for 10 minutes at this temperature. The reaction mixture was treated with saturated aqueous ammonium chloride solution in a conventional manner and then distilled to give cycloheptylbenzene as a colorless oil (8.18 g, but 0.37 g of biphenyl was contained; isolated yield: 90%).

Fourier transform infrared spectroscopy (FTIR) (liquid membrane technique): cm$^{-1}$ 3062, 3027, 2923 (s), 2854 (s), 1602, 1492, 1461, 1451, 1073, 1032, 753 (m), 737 (m), 698 (m);

$^1$H NMR (500 MHz, CDCl$_3$): δ 7.28-7.24 (m, 2H), 7.19-7.12 (m, 3H), 2.68-2.63 (m, 1H), 1.93-1.90 (m, 2H), 1.81-1.78 (m, 2H), 1.67-1.51 (m, 8H); $^{13}$C NMR (125 MHz, CDCl$_3$): δ 150.0, 128.2 (2C), 126.6 (2C), 125.5, 47.1, 36.8 (2C), 27.9 (2C), 27.2 (2C); high resolution mass spectrometry (HRMS) (EI, 70 eV) m/z [M]$^+$Calcd. for C$_{13}$H$_{18}$, 174.1409. Found 174.1418.

Entry No. 17

Cyclohexylbenzene

In a 1-mmol Scale

A mixture of phenyl magnesium bromide (1.25 mL of 0.96-M THF solution, 1.2 mmol) and TMEDA (181.1 μL, 1.2 mmol) was added to a mixture of bromocyclohexane (163.1 mg, 1.0 mmol) and FeCl$_3$ (0.5 mL of 0.1-M THF solution, 5 mol %) at 0° C. over 20 minutes using an injection pump. After the addition of the mixture of Grignard reagent and TMEDA was completed, the reaction mixture was stirred at the temperature for 10 minutes. After treating with saturated aqueous ammonium chloride solution in a conventional manner, the reaction mixture was filtered through a pad of Florisil® and concentrated in vacuum. Using the internal standard (tetrachloroethane, 79 mg, 0.47 mmol), the crude product was analyzed by $^1$H NMR to give cyclohexylbenzene in a yield of 99%. GC analysis gave cyclohexylbenzene in a yield of 99%.

Entry No. 19

1-Cyclohexyl-4-methoxybenzene

The title compound was obtained in a yield of 99% by $^1$H NMR analysis, which was given by comparing with internal standard (tetrachloroethane, 79 mg, 0.47 mmol). Purification by silica gel chromatography gave the title compound as a pale yellow solid (190 mg, yield: 99%).

FTIR (liquid membrane technique): cm$^{-1}$ 3010 (w), 2919 (s), 2850 (m), 1513 (s), 1449 (m), 1248 (s), 1177 (s), 1032 (s), 814 (s);

$^1$H NMR (500 MHz, CDCl$_3$): δ 7.12 (d, J=8.5 Hz, 2H), 6.83 (d, J=8.5 Hz, 2H), 3.78 (s, 3H), 2.50-2.38 (m, 1H), 1.92-1.79 (m, 4H), 1.78-1.65 (m, 1H), 1.45-1.30 (m, 4H), 1.28-1.15 (m, 1H); $^{13}$C NMR (125 MHz, CDCl$_3$): 157.6, 140.3, 127.6 (2C), 113.6 (2C), 55.2, 43.6, 34.7 (2C), 26.9 (2C), 26.1; high resolution mass spectrometry (EI, 70 eV) m/z [M]$^+$Calcd. for C$_{13}$H$_{18}$O$_1$, 190.1358. found 190.1381; Elemental analysis: Calcd. for C$_{13}$H$_{18}$O: C, 82.06; H, 9.53. Found C, 81.80; H, 9.80.

All of the analytical data coincided well with those reported in the literature (Singh et al., Tetrahedron, 2001, 57, 241-247).

Entry No. 20

1-Cyclohexyl-4-methylbenzene

The title compound was obtained in a yield of 98% by $^1$H NMR analysis, which was given by comparing with the internal standard (tetrachloroethane, 79 mg, 0.47 mmol). Purification by silica gel chromatography gave the title compound as a colorless oil (167 mg, yield: 96%).

FTIR (liquid membrane technique): $cm^{-1}$ 3020 (w), 2923 (s), 2852 (m), 1515 (m), 1447 (m), 809 (s);

$^1$H NMR (500 MHz, CDCl$_3$): δ 7.10 (s, 4H), 2.50-2.40 (m, 1H), 2.30 (s, 3H), 1.90-1.79 (m, 4H), 1.78-1.67 (m, 1H), 1.45-1.32 (m, 4H), 1.29-1.17 (m, 1H); $^{13}$C NMR (125 MHz, CDCl$_3$): δ 146.0, 136.0, 129.7 (2C), 127.4 (2C), 44.4, 34.8 (2C), 27.1 (2C), 26.3, 21.1; high resolution mass spectrometry (EI, 70 eV) Z/Z [M]$^+$Calcd. for $C_{13}H_{18}$, 147.1409. Found 147.1388; Elemental analysis: Calcd. for $C_{13}H_{18}$: C, 89.59; H, 10.41. Found C, 89.34; H, 10.64.

All of the analytical data coincided well with those reported in the literature (Yoneharea, F.; Kido, Y.; Sugimoto, H.; Morita, S.; Yamaguchi, M.; *J. Org. Chem.* 2001, 68, 241-247).

Entry No. 21

1-Cyclohexyl-4-trifluoromethylbenzene

The title compound was obtained in a yield of 70% by $^1$H NMR analysis, which was given by comparing with the internal standard (tetrachloroethane, 79 mg, 0.47 mmol). Purification by silica gel chromatography gave the title compound as a colorless oil (153 mg, yield: 67%).

FTIR (liquid membrane technique): $cm^{-1}$ 2927 (m), 2856, 1619, 1451, 1420, 1324 (s), 1162, 1119 (s), 1069 (s), 1017, 830 (s), 656;

$^1$H NMR (500 MHz, CDCl$_3$): δ 7.53 (d, J=8.0 Hz, 2H), 7.31 (d, J=8.0 Hz, 2H), 2.61-2.51 (m, 1H), 1.94-1.74 (m, 5H), 1.48-1.34 (m, 4H), 1.33-1.19 (m, 1H); $^{13}$C NMR (125 MHz, CDCl$_3$): δ 152.1, 128.2 (q, J=32.4 Hz), 127.2 (2C), 124.5 (q, J=270.8 Hz), 125.2 (q, J=3.8 Hz, 2C), 44.5, 34.2 (2C), 26.7 (2C), 26.0; high resolution mass spectrometry (EI, 70 eV) m/z [M]$^+$Calcd. for $C_{13}H_{15}F_3$, 228.1126. Found 228.1144; Elemental analysis: Calcd. for $C_{13}H_{15}F_3$: C, 68.41; H, 6.62. Found C, 68.49; H, 6.83.

Entry No. 22

2-Cyclohexylnaphthalene

2-Naphthyl magnesium bromide (1.46 mL of 0.82 M-THF solution, 1.2 mmol) was added to a mixture of bromocyclohexane (163.1 mg, 1.0 mmol), FeCl$_3$ (0.5 mL of 0.1 M-THF solution, 5 mol %) and TMEDA (181.1 μL, 1.2 mmol) at 25° C. over 20 minutes through an injection pump. After the addition of Grignard reagent mixture was completed, the reaction mixture was stirred for 10 minutes at this temperature. After treating with saturated aqueous ammonium chloride solution in a conventional manner, the reaction mixture was filtered through a pad of Florisil® and concentrated in vacuum. Using the internal standard (tetrachloroethane, 79 mg, 0.47 mmol), the crude product was analyzed by $^1$H NMR to give 2-cyclohexylnaphthalene in a yield of 96%.

Entry No. 23

1-Cyclohexylnaphthalene

The title compound was obtained in a yield of 97%, which was given by $^1$H NMR analysis using the internal standard (tetrachloroethane, 79 mg, 0.47 mmol).

$^1$H NMR (500 MHz, CDCl$_3$): δ 8.11 (br d, J=8.3 Hz, 1H), 7.84-7.81 (m, 1H), 7.67 (br d, J=8.3 Hz, 1H), 7.50-7.36 (m, 4H), 3.35-3.27 (m, 1H), 2.06-1.98 (m, 2H), 1.95-1.86 (m, 2H), 1.86-1.80 (m, 1H), 1.58-1.50 (m, 4H), 1.38-1.27 (m, 1H); $^{13}$C NMR (125 MHz, CDCl$_3$): δ 143.7, 133.9, 131.3, 128.9, 126.2, 125.6, 125.5, 125.2, 123.2, 122.2, 39.2, 34.15 (2C), 27.2 (2C), 26.5; high resolution mass spectrometry (EI, 70 eV) m/z [M]$^+$Calcd. for $C_{16}H_{18}$, 210.1409. Found 210.1433.

Entry No. 24

1-Cyclohexyl-2-methylbenzene

The title compound was obtained in a yield of 98% by $^1$H NMR analysis, which was given by comparing with the internal standard (tetrachloroethane, 79 mg, 0.47 mmol). Purification by silica gel chromatography gave the title compound as a colorless oil (171 mg, yield: 98%).

FTIR (liquid membrane technique): $cm^{-1}$ 3064, 3022, 2925 (s), 2852 (m), 1492, 1448 (m), 741 (s), 723 (s);

$^1$H NMR (500 MHz, CDCl$_3$): δ 7.22-7.05 (m, 4H), 2.75-2.63 (m, 1H), 2.33 (s, 3H), 1.91-1.73 (m, 5H), 1.47-1.34 (m, 4H), 1.33-1.23 (m, 1H); $^{13}$C NMR (125 MHz, CDCl$_3$): δ 145.9, 135.1, 130.1, 126.1, 125.4, 125.3, 40.0, 33.6 (2C), 27.1 (2C), 26.3, 19.3; high resolution mass spectrometry (EI, 70 eV) m/z [M]$^+$Calcd. for $C_{13}H_{18}$, 147.1409. Found 147.1427. Elemental analysis: Calcd. for $C_{13}H_{18}$: C, 89.59; H, 10.41. Found C, 89.56; H, 10.69.

All of the analytical data coincided well with those reported in the literature.

Entry No. 31

1-(Exo-2-norbornyl)-4-methoxybenzene

The title compound was obtained in a yield of 91%, which was given by $^1$H NMR analysis using the internal standard (tetrachloroethane, 79 mg, 0.47 mmol). The diastereomer composition of the product was 95:5 when measured by capillary GC analysis (CHIRALDEX G-TA, manufactured by ASTEC, Inc., 20 m×0.25 mm, 0.125 μm film, 140° C.) (The peaks corresponding to the exo and end isomers of main product were observed in the retention time of 27.9 minutes and 30.4 minutes, respectively).

Analytical data of the compound coincided well with those reported in the literature (Wu, X.-Y.; Xu, H.-D.; Tang, F.-Y.; Zhou, Q.-L. *Tetrahedron Asymmetry* 2001, 12, 2565-2567).

Entry No. 32

1-(4-tert-Butylcyclohexyl)-4-methoxybenzene

The title compound was obtained as a white solid (118.6 mg, isolated yield: 96%). According to capillary GC analysis (CHIRALDEX G-TA, manufactured by ASTEC, Inc., 20 m×0.25 mm, 0.125 μm film, 150° C.), the trans- and cis-products were in a ratio of 96:4 (retention time: 67.4 minutes and 56.2 minutes, respectively).

FTIR (liquid membrane technique): $cm^{-1}$ 2925 (s), 2854 (s), 1611, 1582, 1513 (s), 1486, 1465, 1451, 1393, 1366, 1248 (s), 1181 (m), 1038 (s), 1034 (s), 824 (m), 801 (m);

$^1$H NMR (400 MHz, CDCl$_3$): δ 7.12 (d, J=8.8 Hz, 2H), 6.83 (d, J=8.8 Hz, 2H), 3.78 (s, 3H), 2.42-2.35 (m, 1H), 1.93-1.86 (m, 4H), 1.43-1.35 (m, 2H), 1.18-1.03 (m, 3H), 0.83 (s, 9H); $^{13}$C NMR (100 MHz, CDCl$_3$): δ 157.7, 140.1, 127.7 (2C), 113.7 (2C), 55.2, 47.7, 35.02, 34.4 (2C), 32.6, 27.7 (2C), 27.6 (3C); high resolution mass spectrometry (EI, 70 eV) m/z [M]$^+$Calcd. for $C_{17}H_{26}O_1$ 246.1984. Found 246.1985.

Entry No. 34

Ethyl 6-(4-methoxyphenyl)hexanoate

The title compound was obtained in a yield of 91% by $^1$H NMR analysis, which was given by comparing with the internal standard (tetrachloroethane, 99 mg, 0.57 mmol). Purification by silica gel chromatography gave the title compound as a colorless liquid (220 mg, yield: 88%).

Analytical data of the compound coincided well with those reported in the literature (Lee, J.-Y.; Fu, G. C. *J. Am. Chem. Soc.* 2003, 125, 5616-5617).

Entry No. 35

N-[3-(4-Methoxyphenyl)propyl]indole

The title compound was obtained in a yield of 93% by $^1$H NMR analysis, which was given by comparing with the internal standard (tetrachloroethane, 99 mg, 0.57 mmol). Purification by silica gel chromatography gave the title compound as a colorless oil (231 mg, yield: 87%).

$^1$H NMR (500 MHz, CDCl$_3$): δ 7.63 (d, J=8.0 Hz, 1H), 7.28 (d, J=8.0 Hz, 1H), 7.19 (t, J=8.0 Hz, 1H), 7.12-7.06 (m, 4H), 6.83 (d, J=8.5 Hz, 1H), 6.49 (d, J=3.5 Hz, 1H), 4.10 (t, J=7.0 Hz, 2H), 3.79 (s, 3H), 2.57 (t, J=7.5 Hz, 2H), 2.15 (distorted tt, J=7.5, 7.0 Hz, 2H); $^{13}$C NMR (125 MHz, CDCl$_3$): δ 157.9, 135.9, 132.9, 129.3, 128.5, 127.8, 127.7, 121.3, 120.9, 119.1, 114.1, 113.8, 109.3, 100.96, 55.2, 45.5, 32.0, 31.6; high resolution mass spectrometry (EI, 70 eV) m/z [M]$^+$Calcd. for $C_{18}H_{19}N_1O_1$ 265.1467. Found 265.1478.

Example 4

Production of 2-octylbenzene from Optically Active (S)-2-bromooctane

The same procedures as in Entry No. 15 were carried out, except that (S)-2-bromooctane was used in lieu of bromocycloheptane. Purification by silica gel chromatography gave the title compound as a colorless oil (84.0 mg, yield: 88%). According to the capillary GC analysis (CYCLOSILB, Agilent Technologies, Inc., 30 m×0.25 mm i.d., 0.25 µm film, 80° C. for 120 minutes; and temperature rising rate of oven temperature: 1° C./min.) The enantiomeric excess of the compound was 0% ee. The peaks in the retention time of 125.2 and 129.1 correspond to the optical isomers, respectively, which were observed in a 50:50 ratio.

Following the details given below, EXAMPLES 5 through 8 were carried out.

Materials: Anhydrous tetrahydrofuran (THF), purchased from Kanto Chemical Co., Inc., was distilled from benzophenone ketyl at 760 Torr under an argon atmosphere and immediately provided for use. The water content of the solvent was confirmed with a Karl-Fischer moisture titrator to be less than 20 ppm. FeCl$_3$, purchased from Kanto Chemical Co., Inc., was dehydrated with thionyl chloride to completely dry under reduced pressure, and anhydrous FeCl$_3$ obtained was subsequently stored under an argon atmosphere. By storing at room temperature for several days, 0.1 M THF solution of FeCl$_3$ forms polyether compounds. Thus, the THF solution was provided for use immediately after preparation. ZnCl$_2$, purchased from Aldrich Inc. (anhydrous, beads, 99.99%), was heated under reduced pressure, dried and used immediately thereafter.

The following reagents were prepared in accordance with description of the literature.

ZnCl$_2$.TMEDA: Isobe, M.; Kondo, S.; Nagasawa, N.; Goto, T. *Chem. Lett.* 1977, 679-682

3α-Chlorocholestane: Shoppee, C. W. *J. Chem. Soc.* 1946, 1138

1-(Trimethylsilyl)-5-iodo-pent-1-yne: Koft, E. R.; Smith III, A. B. *J. Org. Chem.* 1984, 49, 832-836

Ethyl 6-iodohexanoate: Leonard, N. J.; Goode, W. E. *J. Am. Chem. Soc.* 1954, 72, 5404-5407

4-Iodobutyronitrile: Newman, M. S.; Closson, R. D. *J. Am. Chem. Soc.* 1944, 66, 1553-1555

Methyl 2,3,4-tri-O-acetyl-6-deoxy-6-iodo-β-D-glucopyranoside: Classon, B.; Liu, Z. *J. Org. Chem.* 1988, 53, 6126-6130

2-Iodoethanal butyl 1,1-dimethyl-2-propenylacetal: Fujioka, T.; Nakamura, T.; Yorimistu, H.; Oshima, K. *Org. Lett.* 2002, 4, 2257-2259

The following reagents were purchased as commercially available ones and used either distilled or recrystallized.

TMEDA (Across), bromocycloheptane (Across), iodocyclohexane (Tokyo Kasei Industry (TCI)), bromocyclohexane (Kanto Chemical), chlorocyclohexane (Tokyo Kasei Industry), ethyl 6-bromohexanoate (Aldrich), 5-bromopentyl acetate (Aldrich), iododecane (Tokyo Kasei Industry), 4-bromo-N-(benzyloxycarbonyl)-piperidine (Aldrich).

The following reagents were used after titration without purification:

4-cyanophenylzinc bromide (0.5 M THF solution, Aldrich), 3-(ethoxycarbonyl)phenylzinc iodide (0.5 M THF solution, Aldrich), 2-pyridylzinc bromide (0.5 M THF solution, Aldrich), trimethylsilylmethylmagnesium chloride (1.0 M Et$_2$O solution, Aldrich).

Instrumentation: Proton nuclear magnetic resonance ($^1$H NMR) and carbon nuclear magnetic resonance ($^{13}$C NMR) were recorded with JEOL ECA-500 (500 MHz) NMR spectrometer. Chemical shifts for hydrogen atoms were reported per million (ppm, δ scale) downfield from tetramethylsilane and were referenced to residual proton in the NMR solvent (CDCl$_3$: δ 7.26). Carbon nuclear magnetic resonance spectra ($^{13}$C NMR) were recorded at 125 or 100 MHz. Chemical shifts for carbons were reported per million (ppm, δ scale) downfield from tetramethylsilane and were referenced to the carbon resonance of the NMR solvent (CDCl$_3$: δ 77.0). The data are presented as follows: chemical shift, multiplicity (s=singlet, d=doublet, t=triplet, q=quartet, m=multiplet and/or multiplet resonances, br=broad), coupling constant (Hertz: Hz), and integration.

Gas chromatographic (GC) analyses were conducted on Shimadzu GC-14B instruments equipped with an FID detector and a capillary column, HR-1 (25 m×0.25 mm i.d., 0.25 µm film). IR spectra were recorded on a React IR 1000 Reaction Analysis System equipped with DuraSample IR (ASI

Reference Example 1

3-Bromocyclohexyl pivaloate and
4-bromocyclohexyl pivaloate

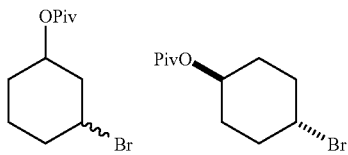

A mixture of 3- and 4-bromocyclohexanols (3.6 g, 20 mmol)(the mixture of 3- and 4-bromocyclohexanols was obtained by treating 1,4-cyclohexanediol with hydrobromic acid (48 wt % in water) under reflux followed by conventional treatments) was treated with pivaloyl chloride (3.7 mL, 30 mmol) in pyridine (50 mL), which was then stirred at room temperature for 4 hours. After evaporation in vacuum, the crude mixture was purified by silica gel chromatography (hexane/ethyl acetate=20/1) to give 3-bromocyclohexyl pivaloate (trans/cis=33/67, 0.63 g, 12%) and trans-4-bromocyclohexyl pivaloate (0.79 g, 15%) as colorless oily substances.

3-Bromocyclohexyl pivaloate: FTIR (neat): $cm^{-1}$ 2956 (m), 2867 (m), 1725 (s), 1480 (w), 1451 (w), 1397 (w), 1366 (w), 1281 (m), 1214 (w), 1152 (s), 1102 (w), 1032 (m), 1011 (w), 951 (w), 888 (w), 772 (w), 702 (w);

$^1$H NMR (500 MHz, $CDCl_3$) trans isomer: δ 5.11-5.06 (m, 1H), 4.41-3.32 (m, 1H), 2.32-2.22 (m, 1H), 2.22-2.13 (m, 1H), 2.12-2.04 (m, 1H), 1.90-1.62 (m, 3H), 1.40-1.25 (m, 2H), 1.20 (s, 9H), cis isomer: δ 4.68-4.60 (m, 1H), 4.00-3.92 (m, 1H), 2.61-2.54 (m, 1H), 2.30-2.22 (m, 1H), 2.00-1.94 (m, 1H), 1.90-1.62 (m, 3H), 1.40-1.25 (m, 2H), 1.18 (s, 9H);

$^{13}$C NMR (125 MHz, $CDCl_3$) trans isomer: δ 177.5, 70.1, 48.5, 41.0, 38.8, 36.5, 29.3, 27.1 (3C), 21.3, cis-isomer: δ 177.7, 70.8, 46.5, 42.9, 38.6, 36.9, 30.2, 27.0 (3C), 23.4; Elemental analysis: Calcd. for $C_{11}H_{19}BrO_2$: C, 50.20; H, 7.28. Found: C, 50.00; H, 7.28

Trans-4-bromocyclohexyl pivaloate: FTIR (neat): $cm^{-1}$ 2958 (m), 2871 (m), 1723 (s), 1480 (w), 1445 (w), 1397 (w), 1368 (w), 1281 (m), 1245 (m), 1152 (s), 1098 (w), 1032 (m), 990 (w), 934 (w), 888 (w), 864 (w), 772 (w), 722 (w), 697 (w), 645 (w); $^1$H NMR (500 MHz, $CDCl_3$): δ 4.90-4.83 (m, 1H), 4.31-4.24 (m, 1H), 2.15-2.00 (m, 4H), 1.97-1.87 (m, 2H), 1.73-1.65 (m, 2H), 1.22 (s, 9H); $^{13}$C NMR (125 MHz, $CDCl_3$): δ 177.8, 68.7, 51.1, 38.8, 32.9 (2C), 28.9 (2C), 27.1 (3C). Elemental analysis: Calcd. for $C_{11}H_{19}BrO_2$: C, 50.20; H, 7.28. Found: C, 49.96; H, 7.32.

Example 5

Entry No. 5-1 to Entry No. 5-8

Following the details given below, effects of various metallic reagents on selectivity and yield of the products were examined.

Unless otherwise indicated, the reaction was proceeded by adding THF solution of $FeCl_3$ (5 mol %) to THF solution of a mixture of bromocycloheptane (1.0 mmol), an organozinc reagent (1.5 equivalents) and TMEDA (1.5 equivalents).

TABLE 4 organozinc reagent (1.5 eq)
FeCl₃ (5 mol %)
TMEDA (1.5 eq)
THF
50° C., 0.5 h

| entry | organozinc reagent | yield (%)[b] 2 | 3 | 4 | 1 |
|---|---|---|---|---|---|
| 5-1[c] | PhMgBr | 96 | 3 | trace | 0 |
| 5-2 | $ZnCl_2$ + 2PhMgBr | 96 | 3 | trace | 0 |
| 5-3 | $ZnCl_2$ + PhMgBr | 0 | trace | trace | >95 |
| 5-4 | PhZnBr (Mg free) | 0 | trace | trace | >95 |
| 5-5[d] | $ZnCl_2$ + PhLi | 0 | trace | trace | >95 |
| 5-6[d] | $ZnCl_2$ + 2PhLi | 0 | trace | trace | >95 |
| 5-7[e] | $ZnCl_2$ + PhMgBr + $Me_3SiCH_2MgCl$ | 95 | 4 | trace | 0 |
| 5-8[f] | $ZnCl_2$ + PhLi + $Me_3SiCH_2MgCl$ | 92 | 7 | 0 | 0 |

[b] The yield is a GC yield corrected by the internal standard (decane).
[c] The reaction was carried out by gradually adding at 0° C. a THF solution of phenylmagnesium bromide and TMEDA to a THF solution of the mixture of FeCl₃ (5 mol %) and bromocyclohexane.
[d] Solvent for THF/Bu₂O (2/1)
[e] Solvent for THF/Et₂O/Bu₂O (2/2/1)
[f] Solvent for THF/pentane/Bu₂O (2/2/1)

Example 6

Entry No. 6-1 Through Entry No. 6-11

Following the details given below, effects of various metallic reagents and halides on yield of the products were examined.

A mixture of $ZnCl_2$·TMEDA (1.5 mmol) and aromatic magnesium reagent shown by ArMgBr (0.8-1.0 M THF solution, 3.0 mmol) was charged and stirred for 0.5 to 1 hour in a dry reactor to give the organozinc reagents shown in TABLE 5 below. The halide (1.0 mmol) given in TABLE 5 below (represented by "(FG)$R_{alkyl}$—X" in TABLE 5) and $FeCl_3$ (0.1 M THF solution, 0.5 mL, 0.05 mmol) were added to the resulting suspension at 0° C. The reaction mixture was stirred at 50° C. for 0.5 hour. The reaction was terminated with saturated aqueous ammonium chloride solution. The reaction mixture was filtered through a pad of Florisil® and concentrated in vacuum. The residue was purified by silica gel chromatography. The other conditions were as described below.

Entry No. 6-1 through Entry No. 6-3
(Phenylcyclohexane)

Entry No. 6-1

Halide: iodocyclohexane (1.0 mmol)
Organozinc reagent: diphenylzinc (1.5 mmol)
Reaction time: 0.5 hour
Colorless oily substance (157 mg, 98%).

Entry No. 6-2

Halide: bromocyclohexane (1.0 mmol)
Organozinc reagent: diphenylzinc (1.5 mmol)

Reaction time: 0.5 hour
Colorless oily substance (155 mg, 97%).

Entry No. 6-3

Halide: chlorocyclohexane (1.0 mmol)
Organozinc reagent: diphenylzinc (1.5 mmol)
Reaction time: 3 hours
Colorless oily substance (141 mg, 88%).
Analytical data of the title compound is reported in Nakamura, M.; Matsuo, K.; Ito, S.; Nakamura, E. *J. Am. Chem. Soc.* 2004, 126, 3686-3687.

Entry No. 6-4 (3-Phenyl-cholestane)

Halide: 3α-chlorocholestane (1.0 mmol)
Organozinc reagent: diphenylzinc (1.5 mmol)
Reaction time: 12 hours
White solid (α/β=14/86, 399 mg, 89%);
FTIR (neat): $cm^{-1}$ 3025 (w), 2925 (s), 2867 (m), 1466 (m), 1447 (m), 1382 (w), 758 (w), 681 (s); $^1$H NMR (500 MHz, CDCl$_3$): δ 7.39-7.13 (m, 5H), 3.11-3.05 (m, 0.14H), 2.59-2.49 (m, 0.86H), 2.09-0.64 (m, 46H); $^{13}$C NMR (125 MHz, CDCl$_3$) β-isomer (main component): δ 147.7, 128.2 (2C), 126.8 (2C), 125.6, 56.6, 56.3, 54.6, 47.0, 44.9, 42.6, 40.1, 39.5, 38.9, 36.6, 36.2, 35.9, 35.7, 35.6, 32.2, 29.9, 28.9, 28.3, 28.0, 24.2, 23.9, 22.9, 22.6, 21.0, 18.7, 12.5, 12.1; Elemental analysis: Calcd. for C$_{33}$H$_{52}$: C, 88.32; H, 11.68. Found: C, 88.12; H, 11.73

Entry No. 6-5 (5-Phenyl-1-(trimethylsilyl)-pent-1-yne)

Halide: 5-iodo-1-(trimethylsilyl)-pent-1-yne (1.0 mmol)
Organozinc reagent: diphenylzinc (1.5 mmol)
Reaction time: 0.5 hour
Colorless oily substance (201 mg, 93%);
FTIR (neat): $cm^{-1}$ 2958 (w), 2902 (w), 2175 (w), 1478 (w), 1451 (s), 1395 (w), 1366 (s), 1268 (w), 1167 (w), 997 (s); $^1$H NMR (500 MHz, CDCl$_3$): δ 7.31-7.25 (m, 3H), 7.21-7.17 (m, 2H), 2.72 (t, J=7.6 Hz, 2H), 2.24 (t, J=7.1 Hz, 2H), 1.84 (tt, J=7.6, 7.1 Hz, 2H), 0.16 (s, 9H); $^{13}$C NMR (125 MHz, CDCl$_3$): δ 141.3, 128.2 (2C), 128.0 (2C), 125.5, 106.8, 87.4, 34.5, 30.0, 19.1, 0.0 (3C); HRMS (EI, 70 eV) m/z [M]$^+$Calcd. for C$_{14}$H$_{20}$Si, 216.1334; Found, 216.1305. Elemental analysis: Calcd. for C$_{14}$H$_{20}$Si: C, 77.71; H, 9.32. Found: C, 77.53; H, 9.13.

Entry No. 6-6 to Entry No. 6-7 (ethyl 6-phenylhexanoate)

Entry No. 6-6

Halide: ethyl 6-iodohexanoate (1.0 mmol)
Organozinc reagent: diphenylzinc (1.5 mmol)
Reaction time: 0.5 hour
Colorless oily substance (218 mg, 99%)

Entry No. 6-7

Halide: ethyl 6-bromohexanoate (1.0 mmol)
Organozinc reagent: diphenylzinc (1.5 mmol)
Reaction time: 0.5 hour
Colorless oily substance (200 mg, 91%)

Analytical data of the title compound is reported in Zhou, J.; Fu, G. C. *J. Am. Chem. Soc.*, 2004, 126, 1340-1341.

Entry No. 6-8 (5-(4-Methylphenyl)pentyl acetate)

Halide: 5-bromopentyl acetate (1.0 mmol)
Organozinc reagent: di(4-methylphenyl)zinc (1.5 mmol)
Reaction time: 0.5 hour
Colorless oily substance (183 mg, 83%);
FTIR (neat): $cm^{-1}$ 3020 (w), 2933 (m), 2866 (w), 1739 (s), 1517 (w), 1463 (w), 1366 (m), 1236 (s), 1044 (m), 805 (m); $^1$H NMR (500 MHz, CDCl$_3$): δ 7.12-7.03 (m, 4H), 4.04 (t, J=6.1 Hz, 2H), 2.57 (t, J=7.8 Hz, 2H), 2.31 (s, 3H), 2.03 (s, 3H), 1.68-1.58 (m, 4H), 1.43-1.34 (m, 2H); $^{13}$C NMR (125 MHz, CDCl$_3$): δ 171.2, 139.3, 135.1, 128.9 (2C), 128.2 (2C), 64.5, 35.3, 31.1, 28.4, 25.5, 21.0 20.9; Elemental analysis: Calcd. for C$_{14}$H$_{20}$O$_2$: C, 76.33; H, 9.15. Found: C, 76.33; H, 9.19.

Entry No. 6-9 (4-(2-Methylphenyl)cyclohexyl pivaloate)

Halide: trans-4-bromo-cyclohexyl pivaloate obtained in REFERENCE EXAMPLE (1.0 mmol)
Organozinc reagent: di(2-methylphenyl)zinc (1.5 mmol)
Reaction time: 0.5 hour
Colorless oily substance (268 mg, 98%, trans/cis=55/45);
FTIR (neat): $cm^{-1}$ 3022 (w), 2937 (m), 2863 (w), 1723 (s), 1480 (w), 1461 (w), 1283 (m), 1162 (s), 1034 (m), 1015 (m), 751 (m), 726 (w); $^1$H NMR (500 MHz, CDCl$_3$) trans isomer: δ 7.21-7.07 (m, 4H), 4.80-4.73 (m, 1H), 2.76-2.70 (m, 1H), 2.33 (s, 3H), 2.12-2.07 (m, 2H), 1.91-1.85 (m, 2H), 1.63-1.41 (m, 4H), 1.20 (s, 9H), cis-isomer: δ 7.24-7.08 (m, 4H), 5.11-5.08 (m, 1H), 2.82-2.74 (m, 1H), 2.35 (s, 3H), 2.05-1.98 (m, 2H), 1.84-1.74 (m, 2H), 1.71-1.62 (m, 4H), 1.26 (s, 9H); $^{13}$C NMR (125 MHz, CDCl$_3$) trans isomer: δ 178.1, 144.1, 135.2, 130.3, 126.2, 125.8, 125.1, 72.5, 38.9, 38.6, 32.1 (2C), 31.3 (2C), 27.1 (3C), 19.3, cis-isomer: δ 177.8, 145.0, 135.1, 120.3, 126.2, 125.7, 125.2, 68.4, 39.1, 39.0, 30.5 (2C), 27.6 (2C), 27.3 (3C), 19.4; Elemental analysis: Calcd. for C$_{18}$H$_{26}$O$_2$: C, 78.79; H, 9.55. Found: C, 78.64; H, 9.54.

Entry No. 6-10 (3-(4-Methoxyphenyl)propionitrile)

Halide: 3-iodopropionitrile (1.0 mmol)
Organozinc reagent: di(4-methoxyphenyl)zinc (1.5 mmol)
Reaction time: 0.5 hour
Colorless oily substance (151 mg, 86%);
FTIR (neat): $cm^{-1}$ 3004 (w), 2937 (w), 2836 (w), 2240 (m), 1611 (w), 1509 (s), 1459 (w), 1301 (w), 1245 (s), 1177 (m), 1109 (w), 832 (m), 809 (m), 700 (w); $^1$H NMR (500 MHz, CDCl$_3$): δ 7.09 (d, J=8.5 Hz, 2H), 6.84 (d, J=8.5 Hz, 2H), 3.77 (s, 3H), 2.70 (t, J=7.5 Hz, 2H), 2.28 (t, J=6.8 Hz, 2H), 1.92 (tt, J=7.5, 6.8 Hz, 2H); $^{13}$C NMR (125 MHz, CDCl$_3$): δ 158.0, 131.5, 129.2 (2C), 119.5, 113.8 (2C), 55.1, 33.2, 26.9, 16.1; Elemental analysis: Calcd. for C$_{11}$H$_{13}$NO: C, 75.40; H, 7.48; N, 7.99. Found: C, 75.29; H, 7.67, N, 7.72

Entry No. 6-11 (Methyl 2,3,4-tri-O-acetyl-6-deoxy-6-[3,4-(methylenedioxy)-phenyl]-β-D-glucopyranoside)

Halide: methyl 2,3,4-tri-O-acetyl-6-deoxy-6-iodo-β-D-glucopyranoside (1.0 mmol)
Organozinc reagent: di[3,4-(methylenedioxy)phenyl]zinc (2.0 mmol) (ZnCl$_2$.TMEDA (2.0 mmol) and ArMgBr (0.8-1.0 M THF solution, 4.0 mmol) were used.)

Reaction time: 0.5 hour
Colorless oily substance (382 mg, 90%);
FTIR (neat): cm$^{-1}$ 1746 (s), 1492 (m), 1443 (m), 1366 (m), 1216 (s), 1030 (s), 928 (m), 809 (w); $^1$H NMR (500 MHz, CDCl$_3$): δ 6.75-6.71 (m, 2H), 6.66-6.62 (m, 1H), 5.93 (s, 2H), 5.44 (t, J=9.5 Hz, 1H), 4.94-4.85 (m, 3H), 3.91 (dt, J=9.5, 2.9 Hz, 1H), 3.11 (s, 3H), 2.78-2.72 (m, 1H), 2.66-2.60 (m, 1H), 2.06 (s, 3H), 2.04 (s, 3H), 2.00 (s, 3H); $^{13}$C NMR (125 MHz, CDCl$_3$): δ 170.1 (2C), 169.8, 147.4, 146.1, 130.1, 122.2, 110.0, 108.0, 101.2, 100.8, 96.2, 72.3, 71.0, 70.3, 69.4, 54.9, 37.1, 20.7 (2C), 20.6; Elemental analysis: Calcd. for C$_{20}$H$_{24}$O$_{10}$: C, 56.60; H, 9.70. Found: C, 56.54; H, 5.97.

Example 7

Entry No. 7-1 to Entry No. 7-6

Following the details given below, effects of various metallic reagents and halides on yield of the products were examined.

A mixture of various aromatic zinc reagents shown by ArZnX (X=Br, I) (0.5 M THF solution, 4.0 mL, 2.0 mmol) and magnesium compounds shown by Me$_3$SiCH$_2$MgCl (1.1 M Et$_2$O solution 1.8 mL, 2.0 mmol) was charged in a dry reactor and stirred at 0° C. for 0.5-1 hour. To the solution

TABLE 5

(FG)R$_{alkyl}$—X $\xrightarrow[\text{THF, 50° C., 0.5 h}]{\text{Ar}_2\text{Zn·TMEDA (1.5 eq)} \atop \text{FeCl}_3 \text{ (5 mol \%)}}$ (FG)R$_{alkyl}$—Ar

| entry | (FG)R$_{alkyl}$—X | organozinc reagent | yield (%) |
|---|---|---|---|
| 6-1 | cyclohexyl–X | Ph$_2$Zn | 98 (X = I) |
| 6-2 | | | 97 (X = Br) |
| 6-3 | | | 88 (X = Cl) |
| 6-4 | cholestanyl-Cl (steroid) | Ph$_2$Zn | 89 |
| 6-5 | Me$_3$Si–C≡C–(CH$_2$)$_3$–I | Ph$_2$Zn | 93 |
| 6-6 | EtO$_2$C–(CH$_2$)$_4$–X | Ph$_2$Zn | 99 (X = I) |
| 6-7 | | | 91 (X = Br) |
| 6-8 | AcO–(CH$_2$)$_4$–Br | (4-Me-C$_6$H$_4$)$_2$Zn | 83 |
| 6-9 | trans-PivO-cyclohexyl-Br | (2-Me-C$_6$H$_4$)$_2$Zn | 98 |
| 6-10 | NC–(CH$_2$)$_3$–I | (4-MeO-C$_6$H$_4$)$_2$Zn | 86 |
| 6-11 | sugar-I (MeO, AcO, OAc, OAc) | (benzo[1,3]dioxol-yl)$_2$Zn | 90 |

In the table, the yield is shown by an isolated yield.

obtained, TMEDA (0.30 mL, 2.0 mmol), various halides (shown by "(FG)R$_{alkyl}$—X" in TABLE 6) (1.0 mmol) and then FeCl$_3$ (0.1 M THF solution, 0.5 mL, 0.05 mmol) were added at 0° C. The reaction mixture was stirred at 30° C. for 6 hours. Saturated NH$_4$Cl aqueous solution was added to terminate the reaction. The mixture was filtered through a pad of Florisil® and concentrated in vacuum. The residue was purified by silica gel chromatography.

Entry No. 7-1 (Ethyl 3-[5-(trimethylsilyl)pent-4-yl]benzoate)

Halide: 5-iodo-1-(trimethylsilyl)-pent-1-yne (1.0 mmol)
Aromatic zinc reagent: 3-(ethoxycarbonyl)phenylzinc iodide (2.0 mmol)
Reaction time: 6 hours
Colorless oily substance (262 mg, 91%)
FTIR (neat): cm$^{-1}$ 2955 (w), 2904 (w), 2175 (m), 1717 (s), 1447 (w), 1365 (w), 1275 (s), 1195 (w), 1105 (m), 1025 (w), 841 (s), 750 (m), 712 (m); $^1$H NMR (500 MHz, CDCl$_3$): δ 7.91-7.86 (m, 2H), 7.41-7.33 (m, 2H), 4.38 (q, J=7.1 Hz, 2H), 2.78 (t, J=7.5 Hz, 2H), 2.24 (t, J=7.1 Hz, 2H), 1.86 (tt, J=7.5, 7.1 Hz, 2H), 1.40 (t, J=6.9 Hz, 3H), 0.18 (s, 9H); $^{13}$C NMR (125 MHz, CDCl$_3$): δ 166.7, 141.8, 133.0, 132.7, 130.5, 129.5, 127.1, 106.7, 85.2, 60.9, 34.4, 30.0, 19.2, 14.3, 0.1 (3C); Elemental analysis: Calcd. for C$_{17}$H$_{24}$O$_2$Si: C, 70.78; H, 8.39. Found: C, 70.64; H, 8.52

Entry No. 7-2 (Ethyl 3-(3-cyanopropyl)benzoate)

Halide: 4-iodobutyronitrile (1.0 mmol)
Aromatic zinc reagent: 3-(ethoxycarbonyl)phenylzinc iodide (2.0 mmol)
Reaction time: 6 hours
Colorless oily substance (156 mg, 72%)
FTIR (neat): cm$^{-1}$ 2981 (w), 2937 (w), 2871 (w), 1713 (s), 1445 (w), 1368 (w), 1277 (s), 1196 (s), 1106 (s), 1084 (m), 1023 (m), 861 (w), 751 (s), 695 (m); $^1$H NMR (500 MHz, CDCl3): δ 7.92-7.84 (m, 2H), 7.38-7.35 (m, 2H), 4.36 (q, J=7.1 Hz, 2H), 2.81 (t, J=7.5 Hz, 2H), 2.32 (t, J=6.9 Hz, 2H), 1.99 (tt, J=7.5, 6.9 Hz, 2H), 1.38 (t, J=7.2 Hz, 3H); $^{13}$C NMR (125 MHz, CDCl$_3$): δ 166.4, 139.9, 132.8, 130.8, 129.2, 128.6, 127.7, 119.2, 60.9, 34.1, 26.7, 16.3, 14.1; Elemental analysis: Calcd. for C$_{13}$H$_{15}$NO$_2$: C, 71.78; H, 6.96, N, 6.45.

Entry No. 7-3 (Ethyl 3-(3-pivaloxycyclohexyl)benzoate)

Halide: 3-bromocyclohexyl pivaloate (trans/cis=33/67, 1.0 mmol) obtained in REFERENCE EXAMPLE 1
Aromatic zinc reagent: 3-(ethoxycarbonyl)phenylzinc iodide (2.0 mmol)
Reaction time: 24 hours
Colorless oily substance (260 mg, 78%, trans/cis=47/53)
FTIR (neat): cm$^{-1}$ 2977 (w), 2937 (w), 2867 (w), 1721 (s), 1283 (m), 1162 (m), 1109 (m), 1028 (w), 754 (w), 654 (w); $^1$H NMR (500 MHz, CDCl$_3$) trans isomer: δ 7.92-7.86 (m, 2H), 7.42-7.33 (m, 2H), 5.21-5.16 (m, 1H), 4.38 (q, J=7.1 Hz, 2H), 3.01-2.92 (m, 1H), 2.08-2.02 (m, 1H), 1.98-1.90 (m, 2H), 1.77-1.67 (m, 3H), 1.58-1.47 (m, 2H), 1.40 (t, J=7.2 Hz, 3H), 1.26 (s, 9H), cis-isomer: δ 7.92-7.87 (m, 2H), 7.43-7.34 (m, 2H), 4.87-4.79 (m, 1H), 4.38 (q, J=7.2 Hz, 2H), 2.77-2.68 (m, 1H), 2.19-2.13 (m, 1H), 2.08-2.01 (m, 1H), 1.97-1.90 (m, 1H), 1.90-1.83 (m, 1H), 1.58-1.33 (m, 4H), 1.40 (t, J=7.2 Hz, 3H), 1.18 (s, 9H); $^{13}$C NMR (125 MHz, CDCl$_3$) trans isomer: δ 177.7, 166.8, 146.8, 131.4, 130.6, 128.4, 127.9, 127.3, 69.3, 60.9, 39.0, 38.4, 37.2, 33.4, 29.3, 27.2 (3C), 21.1, 14.3, cis-isomer: δ 177.9, 166.7, 146.1, 131.4, 130.6, 128.4, 127.8, 127.4, 72.5, 60.9, 42.4, 39.1, 38.6, 32.9, 31.2, 27.1 (3C), 24.1, 14.3; Elemental analysis: Calcd. for C$_{20}$H$_{28}$O$_4$: C, 72.26; H, 8.49.

Entry No. 7-4 (4-Cyclohexylbenzonitrile)

Halide: 3-bromocyclohexane (1.0 mmol)
Aromatic zinc reagent: 4-cyanophenylzinc bromide (2.0 mmol)
Reaction time: 6 hours
Colorless oily substance (167 mg, 90%)
FTIR (neat): cm$^{-1}$ 2925 (s), 2852 (m), 2227 (m), 1607 (m), 1505 (m), 1449 (m), 1415 (w), 1177 (w), 1000 (w), 823 (s); $^1$H NMR (500 MHz, CDCl$_3$): δ 7.56 (d, J=8.6 Hz, 2H), 7.30 (d, J=8.6 Hz, 2H), 2.12-2.00 (m, 1H), 1.92-1.80 (m, 4H), 1.80-1.69 (m, 1H), 1.47-1.33 (m, 4H), 1.33-1.20 (m, 1H); $^{13}$C NMR (125 MHz, CDCl$_3$): δ 153.4, 132.1 (2C), 127.6 (2C), 119.1, 109.5, 44.7, 33.9 (2C), 26.6 (2C), 25.9; Elemental analysis: Calcd. for C$_{13}$H$_{15}$N: C, 84.28; H, 8.16; N, 7.56. Found: C, 84.12; H, 8.36; N, 7.36.

Entry No. 7-5 (4-(4-Cyanophenyl)-N-(benzyloxycarbonyl)piperidine)

Halide: 4-bromo-N-(benzyloxycarbonyl)piperidine) (1.0 mmol)
Aromatic zinc reagent: 4-cyanophenylzinc bromide (2.0 mmol)
Reaction time: 6 hours
Pale yellow solid (253 mg, 79%)
FTIR (neat): cm$^{-1}$ 3014 (w), 2943 (w), 2923 (w), 2856 (w), 2227 (m), 1688 (s), 1466 (m), 1455 (m), 1436 (m), 1273 (w), 1218 (s), 1125 (m), 1057 (m), 1009 (m), 917 (w), 838 (m), 760 (s), 702 (s); $^1$H NMR (500 MHz, CDCl$_3$): δ 7.59 (d, J=8.6 Hz, 2H), 7.39-7.26 (m, 7H), 5.16 (br s, 2H), 4.35 (br s, 2H), 2.89 (br s, 2H), 1.90-1.78 (m, 2H), 1.70-1.58 (m, 2H); $^{13}$C NMR (125 MHz, CDCl$_3$): δ 155.2, 150.8, 136.7, 132.4 (2C), 128.5 (2C), 128.0, 127.9 (2C), 127.6 (2C), 118.8, 110.3, 67.2, 44.3 (2C), 42.7, 32.6 (2C); Elemental analysis: Calcd. for C$_{20}$H$_{20}$N$_2$O$_2$: C, 74.98; H, 6.29. N, 8.74. Found: C, 74.80; H, 6.42, N, 8.54.

Entry No. 7-6 (2-Pyridyldecane)

Halide: iododecane (1.0 mmol)
Aromatic zinc reagent: 2-pyridylzinc bromide (1.5 mmol)
Reaction time: 0.5 hour
Colorless oily substance (215 mg, 98%)
FTIR (neat): cm$^{-1}$ 2923 (s), 2854 (s), 1590 (m), 1569 (w) 1468 (m), 1434 (m), 1148 (w), 1050 (w), 994 (w), 747 (s); $^1$H NMR (500 MHz, CDCl$_3$): δ 8.52 (d, J=4.6 Hz, 1H) 7.58 (td, J=7.6, 1.8 Hz, 1H) 7.14 (d, J=7.5 Hz, 1H) 7.09 (dd, J=6.9, 4.9 Hz, 3H), 2.78 (t, J=7.7 Hz, 2H), 1.75-1.68 (m, 2H), 1.40-1.25 (m, 14H), 0.89 (t, J=6.9 Hz, 3H); $^{13}$C NMR (125 MHz, CDCl$_3$): δ 162.5, 149.2, 136.2, 122.7, 120.8, 38.4, 31.9, 29.9, 29.6, 29.5 (2C), 29.4, 29.3, 22.7, 14.1; Elemental analysis: Calcd. for C$_{15}$H$_{25}$N: C, 82.13; H, 11.49; N, 6.38. Found: C, 82.01; H, 11.39; 6.19.

TABLE 6

(FG)R$_{alkyl}$—X $\xrightarrow[\text{THF, 30° C., 6 h}]{\substack{\text{(FG)ArZnCH}_2\text{SiMe}_3 \text{ (2.0 eq)} \\ \text{FeCl}_3 \text{ (5 mol \%)} \\ \text{TMEDA (2.0 eq)}}}$ (FG)R$_{alkyl}$—Ar(FG)

| entry | (FG)R$_{alkyl}$—X | organozinc reagent | yield (%) |
|---|---|---|---|
| 7-1 | Me$_3$Si—C≡C—CH$_2$CH$_2$CH$_2$—I | 3-(EtO$_2$C)C$_6$H$_4$—ZnL | 91 |
| 7-2 | NC—CH$_2$CH$_2$CH$_2$—I | 3-(EtO$_2$C)C$_6$H$_4$—ZnL | 72 |
| 7-3 | PivO-cyclohexyl-Br | 3-(EtO$_2$C)C$_6$H$_4$—ZnL | 78 |
| 7-4 | cyclohexyl-Br | 4-(NC)C$_6$H$_4$—ZnL | 90 |
| 7-5 | N-Cbz-4-bromopiperidine | 4-(NC)C$_6$H$_4$—ZnL | 79 |
| 7-6 | n-C$_{10}$H$_{21}$—I | 2-pyridyl—ZnL | 98 |

In the table, L represents CH$_2$SiMe$_3$.
In the table, the yield is shown by an isolated yield.

Example 8

Entry No. 8-1 (5-Butoxy-2,2-dimethyl-3-(phenylmethyl)tetrahydrofuran)

The title compound was obtained in a manner similar to Entry No. 6-1, except that diphenylzinc (1.5 mmol) was used as the organozinc reagent and 2-iodoethanal butyl 1,1-dimethyl-2-propenyl acetate (1.0 mmol) was used as the halide (Procedure A). Colorless oily substance (198 mg, 76%).

FTIR (neat): cm$^{-1}$ 3008 (w), 2962 (m), 2933 (m), 2873 (m), 1455 (w), 1366 (w), 1328 (w), 1246 (w), 1096 (s), 1034 (s), 980 (s), 911 (w), 836 (w); 726 (m), 699 (s); $^1$H NMR (500 MHz, CDCl$_3$) trans isomer: δ 7.30-7.26 (m, 2H), 7.21-7.15 (m, 3H), 4.97 (d, J=4.6 Hz, 1H), 3.65 (dt, J=9.7, 6.9 Hz, 1H), 3.30 (dt, J=9.7, 6.9 Hz, 1H), 2.74-2.66 (m, 1H), 2.50-2.40 (m, 2H), 1.94-1.87 (m, 1H), 1.82-1.72 (m, 1H), 1.55-1.45 (m, 2H), 1.38-1.26 (m, 2H), 1.30 (s, 3H), 1.13 (s, 3H), 0.89 (t, J=7.2 Hz, 3H), cis-isomer: δ 7.31-7.25 (m, 2H), 7.22-7.14 (m, 3H), 5.03-4.99 (m, 1H), 3.71 (dt, J=9.7, 6.9 Hz, 1H), 3.34 (dt, J=9.7, 6.9 Hz, 1H), 2.75-2.68 (m, 1H), 2.57-2.49 (m, 1H), 2.27-2.18 (m, 1H), 2.12-2.04 (m, 1H), 1.78-1.65 (m, 1H), 1.60-1.48 (m, 2H), 1.44-1.32 (m, 2H), 1.26 (s, 3H), 1.23 (s, 3H), 0.92 (t, J=7.2 Hz, 3H); $^{13}$C NMR (125 MHz, CDCl$_3$) trans isomer: δ 140.8, 128.7 (2C), 128.3 (2C), 126.0, 101.7, 83.4, 66.6, 47.6, 40.0, 36.4, 31.8, 29.7, 23.8, 19.4, 13.9, cis-isomer: δ 140.9, 128.6 (2C), 128.4 (2C), 126.0, 103.0, 82.7, 67.7, 50.3, 39.0, 36.6, 31.9, 28.0, 23.2, 19.4, 13.9; Elemental analysis: Calcd. for C$_{17}$H$_{26}$O$_2$: C, 77.82; H, 9.99. Found: C, 77.69; H, 10.02.

Entry No. 8-2 (5-Butoxy-2,2-dimethyl-3-[3,4-(methylenedioxy)phenyl-methyl]tetrahydrofuran)

The title compound was obtained in a manner similar to Entry No. 6-1, except for using di[3,4-(methylenedioxy)phenyl]zinc (1.5 mmol) as the organozinc reagent and 2-iodoethanal butyl 1,1-dimethyl-2-propenyl acetate (1.0 mmol) as the halide (Procedure A). Colorless oily substance (264 mg, 86%);

FTIR (neat): cm$^{-1}$ 2964 (m), 2935 (m), 2875 (m), 1505 (m), 1490 (s), 1441 (m), 1366 (w), 1245 (s), 1191 (w), 1096 (s), 1036 (s), 980 (s), 924 (m), 812 (w); $^1$H NMR (500 MHz, CDCl$_3$) trans isomer: δ 6.71 (d, J=8.0 Hz, 1H), 6.69 (s, 1H), 6.61 (d, J=8.0 Hz, 1H), 5.92 (s, 2H), 4.96 (d, J=5.2 Hz, 1H), 3.65 (dt, J=9.2, 6.6 Hz, 1H), 3.30 (dt, J=9.2, 6.6 Hz, 1H), 2.68-2.59 (m, 1H), 2.43-2.34 (m, 2H), 1.94-1.87 (m, 1H), 1.80-1.69 (m, 1H), 1.56-1.46 (m, 2H), 1.38-1.27 (m, 2H), 1.30 (s, 3H), 1.11 (s, 3H), 0.89 (t, J=7.4 Hz, 3H), cis-isomer: δ 6.72 (d, J=8.0 Hz, 1H), 6.66 (s, 1H), 6.61 (d, J=8.0 Hz, 1H), 5.92 (s, 2H), 5.03-4.98 (m, 1H), 3.71 (dt, J=9.7, 6.9 Hz, 1H), 3.34 (dt, J=9.7, 6.9 Hz, 1H), 2.66-2.57 (m, 1H), 2.48-2.40 (m, 1H), 2.27-2.18 (m, 1H), 2.07-1.97 (m, 1H), 1.78-1.67 (m, 1H), 1.60-1.47 (m, 2H), 1.43-1.30 (m, 2H), 1.24 (s, 3H), 1.23 (s, 3H), 0.92 (t, J=7.2 Hz, 3H); $^{13}$C NMR (125 MHz, CDCl$_3$) trans isomer: δ 147.5, 145.7, 134.6, 121.5, 109.1, 108.1, 101.7, 100.8, 83.3, 66.6, 47.8, 38.9, 36.1, 31.8, 29.7, 23.8, 19.4, 13.9, cis-isomer: δ 147.5, 145.7, 134.7, 121.4, 109.0, 108.1, 103.0, 100.8, 82.6, 67.7, 50.4, 39.0, 36.2, 31.9, 28.0, 23.2, 19.4, 13.8; Elemental analysis: Calcd. for C$_{18}$H$_{26}$O$_4$: C, 70.56; H, 8.55. Found: C, 70.28; H, 8.60

Entry No. 8-3 (5-Butoxy-2,2-dimethyl-3-(4-cyanophenylmethyl)tetrahydrofuran)

The title compound was obtained in a manner similar to Entry No. 7-1, except for using 4-cyanophenylzinc bromide (2.0 mmol) as the aromatic zinc reagent and 2-iodoethanal butyl 1,1-dimethyl-2-propenyl acetate (1.0 mmol) as the halide and changing the reaction time to 24 hours (Procedure B). Colorless oily substance (210 mg, 73%);

FTIR (neat): cm$^{-1}$ 2962 (m), 2933 (m), 2871 (w), 2229 (m), 1609 (m), 1451 (w), 1366 (w), 1328 (w), 1246 (w), 1094 (s), 1034 (s), 978 (s), 911 (w), 854 (m), 822 (m), 764 (w); $^1$H NMR (500 MHz, CDCl$_3$) trans isomer: δ 7.58 (d, J=8.2 Hz, 2H), 7.29 (d, J=8.6 Hz, 2H), 4.97 (d, J=4.6 Hz, 1H), 3.65 (dt, J=9.2, 6.6 Hz, 1H), 3.30 (dt, J=9.2, 6.6 Hz, 1H), 2.82-2.74 (m, 1H), 2.55-2.39 (m, 2H), 1.87-1.83 (m, 1H), 1.80-1.72 (m, 1H), 1.56-1.46 (m, 2H), 1.38-1.27 (m, 2H), 1.32 (s, 3H), 1.13 (s, 3H), 0.89 (t, J=7.4 Hz, 3H), cis-isomer: δ 7.58 (d, J=8.0 Hz, 2H), 7.29 (d, J=8.6 Hz, 2H), 5.04-4.98 (m, 1H), 3.71 (dt, J=9.2, 6.9 Hz, 1H), 3.34 (dt, J=9.2, 6.9 Hz, 1H), 2.82-2.74 (m, 1H), 2.66-2.58 (m, 1H), 2.22-2.13 (m, 1H), 2.12-2.04 (m, 1H), 1.75-1.68 (m, 1H), 1.65-1.45 (m, 2H), 1.43-1.25 (m, 2H), 1.25 (s, 3H), 1.22 (s, 3H), 0.92 (t, J=7.2 Hz, 3H); $^{13}$C NMR (125 MHz, CDCl$_3$) trans isomer: δ 146.4, 132.2 (2C), 129.5 (2C), 118.9, 110.0, 101.6, 83.2, 66.6, 47.3, 38.7, 36.6, 31.7, 29.6, 23.8, 19.3, 13.8, cis-isomer: δ 146.5, 132.1 (2C), 129.4 (2C), 118.8, 109.8, 102.7, 82.5, 67.5, 49.5, 38.5, 36.6, 31.7, 28.0, 23.2, 19.2, 13.7; Elemental analysis: Calcd. for C$_{18}$H$_{25}$NO$_2$: C, 75.22; H, 8.77; N, 4.87. Found: C, 75.04; H, 8.84; N, 4.72.

TABLE 7

| entry | organozinc reagent | procedure | yield (%) |
|---|---|---|---|
| 8-1 | phenyl | A | 76% (63/37) |
| 8-2 | 3,4-methylenedioxyphenyl-methyl | A | 86% (64/36) |
| 8-3 | 4-cyanophenyl | B | 73% (63/37) |

In the table, the yield is shown by an isolated yield.

Example 9

Entry No. 9-1 Through Entry No. 9-15

Following the details given below, effects of Lewis acid metal salts on the cross-coupling reaction were examined.

Cycloheptane bromide 1 and 20 mol % of Lewis acid metal salt shown in TABLE 8 below were added to diphenylzinc reagent prepared from zinc chloride-TMEDA complex and 2 equivalents of phenyl lithium. Then, 5 mol % of iron chloride was added to the mixture at 0° C. After stirring at 50° C. for an hour, saturated ammonium chloride aqueous solution was added to the mixture to terminate the reaction. Analysis was made by GC and the yield was calculated by comparing with internal standard n-decane (TABLE 8).

TABLE 8

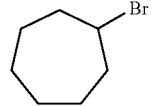

| entry | Lewis acid metal salt | conditions | GC yield (%) 2 | 3 | 4 | 1 |
|---|---|---|---|---|---|---|
| 9-1 | $MgBr_2$ | freshly prepared before use | >98 | trace | trace | 0 |
| 9-2 | $CaCl_2$ | without further purification | 0 | trace | trace | >98 |
| 9-3 | $BF_3 \cdot OEt_2$ | without further purification | 6 | 3 | 3 | <90 |
| 9-4 | $BEt_3$ | 1.0-M solution in hexane | 0 | 1 | 1 | >95 |
| 9-5 | $Me_3SiCl$ | distilled before use | 3 | 6 | 2 | <90 |
| 9-6 | $SnCl_4$ | 1.0-M solution in heptane | 0 | 2 | 2 | >95 |
| 9-7 | $CuCl_2$ | dried (120° C., 1 h, <0.5 mmHg) | 0 | 2 | 3 | >95 |
| 9-8 | $TiCl_4$ | 1.0-M solution in toluene | >98 | 1 | trace | <1 |
| 9-9 | $ZrCl_4$ | dried (120° C., 1 h, <0.5 mmHg) | 90 | trace | trace | 10 |
| 9-10 | $HfCl_4$ | dried (120° C., 1 h, <0.5 mmHg) | 76 | 1 | 1 | 11 |
| 9-11 | $AlCl_3$ | without further purification | 85 | trace | trace | 12 |
| 9-12 | $Ga_2Cl_4$ | dried (80° C., 1 h, <0.5 mmHg) | 10 | 4 | 5 | 77 |
| 9-13 | $InCl_3$ | dried (120° C., 5 h, <0.5 mmHg) | 0 | trace | trace | >98 |
| 9-14 | $CeCl_3$ | dried (90° C., 5 h, <0.5 mmHg) | 1 | 1 | 3 | >95 |
| 9-15 | $SmI_2$ | 1.0-M solution in THF | 0 | trace | trace | >98 |

In Entry No. 9-2, the reaction was carried out using halides of calcium belonging to the same group as in magnesium. However, no cross-coupling reaction occurred at all but the starting materials were recovered quantitatively. Trifluoroborane-diethyl ether complex, triethylborane, chlorotrimethylsilane, tin (IV) chloride and copper (II) chloride, which are representative of Lewis acids used for Aldol reaction, etc., were tested. They hardly exhibited catalytic activities but only the starting materials were recovered (Entry No. 9-3 through Entry No. 9-7).

Where metal halides of Group IV were used, the reaction was accelerated to give Coupled Product 2 in a good yield. The catalytic activity was found in the order of titanium>zirconium>hafnium (Entry No. 9-8 through Entry No. 9-10). Further when aluminum chloride was added, the cross-coupling reaction proceeded smoothly though the starting materials remain slightly (Entry No. 9-11). Also, gallium of the same group exhibited the catalytic activity, albeit only slightly. However, indium of the same group showed no catalytic activity (Entry No. 9-12, Entry No. 9-13). In lanthanoids frequently used as Lewis acids, cerium (III) chloride and samarium iodide were tested but failed to show any catalytic activity at all.

The foregoing testing reveals that chlorides of the group IV metals and aluminum (III) chloride had a good catalytic activity, in addition to magnesium bromide. In particular, titanium (IV) chloride exhibited its catalytic activity comparable to magnesium.

Example 10

2,4-Diphenylpentane

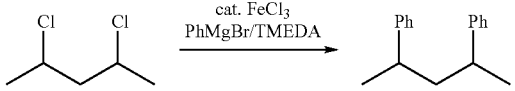

A mixture of phenyl magnesium bromide (1.25 mL of 0.96 M THF solution, 1.2 mmol) and TMEDA (181.1 μL, 1.2 mmol) was added to a solution of 2,4-dichloropentane (70.5 mg, 0.5 mmol) and $FeCl_3$ (0.5 mL of 0.1 M THF solution, 0.05 mmol) in THF (0.5 mL) at 50° C. over an hour through a syringe pump. The resulting mixture was stirred at the temperature for 20 minutes and saturated ammonium chloride aqueous solution was added thereto to terminate the reaction, followed by diluting with 3 mL of ethyl acetate. The dilution was filtered through a packed silica gel (eluent: ethyl acetate) followed by concentration under reduced pressure. $^1$H NMR analysis indicates that the desired product was obtained in almost quantitative yield. Purification by recycling GPC gave the pure compound in a yield of 71%.

$^1$H NMR of a 1:1 diastereomer mixture (500 MHz, $CDCl_3$) δ 1.16 (d, J=6.9 Hz, 3H, $CH_3$ for one diastereomer), 1.23 (d, J=6.9 Hz, 3H, $CH_3$ of the other diastereomer), 1.76 (distorted dt, J=13.2, 7.4 Hz, 0.5H, CHH for another diastereomer), 1.87 (t, J=7.4 Hz, 1H, $CH_2$ for another diastereomer), 1.94 (distorted dt, J=13.2, 7.4 Hz, 0.5H, —CHH— for one diastereomer), 2.48 (sextet, J=7.4 Hz, 1H, CHPh for another diastereomer), 2.64 (sextet, J=7.4 Hz, 1H, CHPh for another diastereomer), 7.10-7.21 (m, 6H, aromatic protons for both diastereomers), 7.26-7.31 (m, 4H, aromatic protons for both diastereomers). EI-MS (70 eV) m/z [M]$^+$+Calcd. for $C_{17}H_{20}$, 224.2. Found 224.0

Example 11

2,4,6-Triphenylheptane

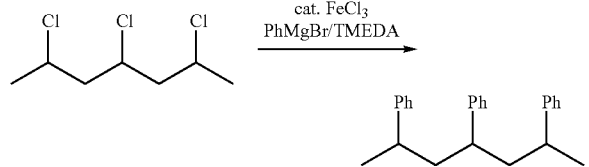

A mixture of phenyl magnesium bromide (1.25 mL of a 0.96-M THF solution, 1.2 mL) and TMEDA (181.1 μL, 1.2 mmol) was added to a THF solution of a mixture of 2,4,6-trichloroheptane (67 mg, 0.33 mmol) and FeCl$_3$ (0.5 mL of a 0.1-M THF solution, 0.05 mmol) at 50° C. for 5 hours through a syringe pump. The resulting mixture was stirred at the temperature for 20 minutes. After saturated ammonium chloride aqueous solution was added to terminate the reaction, the mixture was diluted with 3 mL of ethyl acetate. The dilution was filtered through packed silica gel (eluent; ethyl acetate) and concentrated under reduced pressure. The pure product was obtained in a yield of 65% (flash chromatography, eluent: hexane).

$^1$H NMR of a mixture of 3 diastereomers (500 MHz, CDCl$_3$) δ 1.04 (d, J=6.9 Hz, 1.0H) 1.05 (d, J=6.9 Hz, 1.4H), 1.12 (d, J=6.9 Hz, 1.8H), 1.15 (d, J=6.9 Hz, 1.8H), 1.69-2.01 (m, 4H), 2.30-2.62 (m, 3H), 6.96-7.31 (m, 15H, aromatic protons), EI-MS (70 eV) m/z [M]+Calcd. for $C_{25}H_{28}$, 328.2. Found 327.9.

The invention claimed is:

1. A process for production of an aromatic compound represented by formula (1) below:

R-A          (1)

wherein, R is an optionally substituted hydrocarbon group or a $C_3$-$C_{10}$ saturated or unsaturated ring group, which ring may optionally be intervened by an oxygen atom or a group represented by formula —N(B)— (wherein B is a hydrogen atom, an optionally substituted $C_1$-$C_{10}$ hydrocarbon group or an optionally substituted $C_1$-$C_{10}$ alkoxycarbonyl group) and may optionally be substituted;

with the proviso that an aromatic group or a heteroaromatic group is excluded from R; and A is an optionally substituted $C_4$-$C_{20}$ aromatic group or an optionally substituted heteroaromatic group, which comprises reacting a compound represented by formula (2) below:

R—X          (2)

wherein, R has the same significance as defined above, and X is a halogen atom or a sulfonic acid ester, with an aromatic magnesium reagent represented by formula (3a) below:

A-Mg—Y$^1$          (3a)

wherein A has the same significance as defined above and Y$^1$ is bromine, iodine, chlorine or a carbanion ligand, in the presence of an iron catalyst and a diamine compound.

2. The process for production of an aromatic compound according to claim 1, wherein the iron catalyst is an iron salt or an iron complex.

3. The process for production of an aromatic compound according to claim 1, wherein the diamine compound is a bidentate ligand.

4. The process for production of an aromatic compound according to claim 1, wherein R is an optionally substituted primary alkyl group or an optionally substituted secondary alkyl group.

5. The process for production of an aromatic compound according to claim 1, wherein A is an optionally substituted $C_4$-$C_{20}$ aryl group.

6. A process for production of an aromatic compound represented by formula (1) below:

R-A          (1)

wherein, R is an optionally substituted hydrocarbon group or a $C_3$-$C_{10}$ saturated or unsaturated ring group, which ring may optionally be intervened by an oxygen atom or a group represented by formula —N(B)— (wherein B is a hydrogen atom, an optionally substituted $C_1$-$C_{10}$ hydrocarbon group or an optionally substituted $C_1$-$C_{10}$ alkoxycarbonyl group) and may optionally be substituted;

with the proviso that an aromatic group or a heteroaromatic group is excluded from R; and A is an optionally substituted $C_4$-$C_{20}$ aromatic group or an optionally substituted heteroaromatic group, which comprises:

a step of reacting an aromatic magnesium reagent represented by formula (3a) below:

A-Mg—Y$^1$          (3a)

wherein A has the same significance as defined above and Y$^1$ is bromine, iodine, chlorine or a carbanion ligand, with a zinc compound represented by formula (4b) below:

Z$^3$—Zn—Z$^4$          (4b)

wherein each of Z$^3$ and Z$^4$, which may be the same or different, independently represents bromine, iodine, chlorine, fluorine or a trifluoromethanesulfonyl group, in the presence of a diamine compound to give the reaction mixture; and a step of reacting the reaction mixture with a compound represented by formula (2) below:

R—X          (2)

wherein R has the same significance as defined above and X is a halogen atom or a sulfonic acid ester, in the presence of an iron catalyst.

7. The process for production of an aromatic compound according to claim 6, wherein the iron catalyst is an iron salt or an iron complex.

8. The process for production of an aromatic compound according to claim 6, wherein the diamine compound is a bidentate ligand.

9. The process for production of an aromatic compound according to claim 6, wherein R is an optionally substituted primary alkyl group or an optionally substituted secondary alkyl group.

10. The process for production of an aromatic compound according to claim 6, wherein A is an optionally substituted $C_4$-$C_{20}$ aryl group.

11. A process for production of an aromatic compound represented by formula (1) below:

$$R\text{-}A \tag{1}$$

wherein, R is an optionally substituted hydrocarbon group or a $C_3$-$C_{10}$ saturated or unsaturated ring group, which ring may optionally be intervened by an oxygen atom or a group represented by formula —N(B)— (wherein B is a hydrogen atom, an optionally substituted $C_1$-$C_{10}$ hydrocarbon group or an optionally substituted $C_1$-$C_{10}$ alkoxycarbonyl group) and may optionally be substituted;

with the proviso that an aromatic group or a heteroaromatic group is excluded from R; and A is an optionally substituted $C_4$-$C_{20}$ aromatic group or an optionally substituted heteroaromatic group, which comprises:

a step of reacting an aromatic lithium reagent represented by formula (3c) below:

$$A\text{-}Li \tag{3c}$$

wherein A has the same significance as defined above, with a zinc compound represented by formula (4b) below:

$$Z^3\text{—}Zn\text{—}Z^4 \tag{4b}$$

wherein each of $Z^3$ and $Z^4$, which may be the same or different, independently represents bromine, iodine or chlorine, in the presence of a diamine compound and then reacting with a Lewis acid metal compound containing at least one metal selected from magnesium, titanium, zirconium, hafnium, gallium and aluminum to give the reaction mixture, and a step of reacting the reaction mixture with a compound represented by formula (2) below:

$$R\text{—}X \tag{2}$$

wherein R has the same significance as defined above and X is a halogen atom or a sulfonic acid ester, in the presence of an iron catalyst.

12. The process for production of an aromatic compound according to claim 11, wherein the iron catalyst is an iron salt or an iron complex.

13. The process for production of an aromatic compound according to claim 11, wherein the diamine compound is a bidentate ligand.

14. The process for production of an aromatic compound according to claim 11, wherein R is an optionally substituted primary alkyl group or an optionally substituted secondary alkyl group.

15. The process for production of an aromatic compound according to claim 11, wherein A is an optionally substituted $C_4$-$C_{20}$ aryl group.

16. The process for production of an aromatic compound according to claim 11, wherein the Lewis acid metal compound is a metal compound represented by formula (4c) below:

$$M(Z^1)_n \tag{4c}$$

wherein M is magnesium, titanium, zirconium, hafnium, gallium or aluminum; each of $Z^1$, which may be the same or different, independently represents bromine, iodine, chlorine or a carbanion ligand; and n is an integer of 2 to 4.

17. A process for production of an aromatic compound represented by formula (1) below:

$$R\text{-}A \tag{1}$$

wherein, R is an optionally substituted hydrocarbon group or a $C_3$-$C_{10}$ saturated or unsaturated ring group, which ring may optionally be intervened by an oxygen atom or a group represented by formula —N(B)— (wherein B is a hydrogen atom, an optionally substituted $C_1$-$C_{10}$ hydrocarbon group or an optionally substituted $C_1$-$C_{10}$ alkoxycarbonyl group) and may optionally be substituted;

with the proviso that an aromatic group or a heteroaromatic group is excluded from R; and A is an optionally substituted $C_4$-$C_{20}$ aromatic group or an optionally substituted heteroaromatic group, which comprises:

a step of reacting an aromatic zinc reagent represented by formula (3b) below:

$$A\text{-}Zn\text{—}Y^2 \tag{3b}$$

wherein A has the same significance as defined above and $Y^2$ is bromine, iodine or chlorine, with a magnesium compound represented by formula (4a) below:

$$Z^1\text{—}Mg\text{—}Z^2 \tag{4a}$$

wherein $Z^1$ is a carbanion ligand and $Z^2$ is bromine, iodine or chlorine] in the presence of a diamine compound to give the reaction mixture; and a step of reacting the reaction mixture with a compound represented by formula (2) below:

$$R\text{—}X \tag{2}$$

wherein R has the same significance as defined above and X is a halogen atom or a sulfonic acid ester, in the presence of an iron catalyst.

18. The process for production of an aromatic compound according to claim 17, wherein the iron catalyst is an iron salt or an iron complex.

19. The process for production of an aromatic compound according to claim 17, wherein the diamine compound is a bidentate ligand.

20. The process for production of an aromatic compound according to claim 17, wherein R is an optionally substituted primary alkyl group or an optionally substituted secondary alkyl group.

21. The process for production of an aromatic compound according to claim 17, wherein A is an optionally substituted $C_4$-$C_{20}$ aryl group.

* * * * *